United States Patent
Bahrami

(10) Patent No.: US 11,072,638 B2
(45) Date of Patent: Jul. 27, 2021

(54) IMMUNOSTIMULATING PEPTIDES

(71) Applicant: AIMVION A/S, Copenhagen N. (DK)

(72) Inventor: Shervin Bahrami, Tilst (DK)

(73) Assignee: Aimvion A/S, Aarhus (DK)

( * ) Notice: Subject to any disclaimer, the term of this patent is extended or adjusted under 35 U.S.C. 154(b) by 0 days.

(21) Appl. No.: 16/327,135

(22) PCT Filed: Aug. 23, 2017

(86) PCT No.: PCT/EP2017/071228
§ 371 (c)(1),
(2) Date: Feb. 21, 2019

(87) PCT Pub. No.: WO2018/037042
PCT Pub. Date: Mar. 1, 2018

(65) Prior Publication Data
US 2019/0194278 A1    Jun. 27, 2019

(30) Foreign Application Priority Data

Aug. 23, 2016  (DK) .......................... PA 2016 70634
Sep. 30, 2016  (WO) ................ PCT/DK2016/050316
Apr. 5, 2017   (EP) .................................... 17165139

(51) Int. Cl.
| | | |
|---|---|---|
| *C07K 14/47*   | (2006.01) |
| *C07K 14/15*   | (2006.01) |
| *C07K 14/005*  | (2006.01) |
| *A61K 47/62*   | (2017.01) |
| *A61P 37/04*   | (2006.01) |
| *A61P 35/00*   | (2006.01) |
| *A61K 38/17*   | (2006.01) |
| *A61K 45/06*   | (2006.01) |
| *C07K 16/18*   | (2006.01) |
| *A61K 38/00*   | (2006.01) |
| *A61K 39/00*   | (2006.01) |

(52) U.S. Cl.
CPC ...... *C07K 14/4705* (2013.01); *A61K 38/1709* (2013.01); *A61K 45/06* (2013.01); *A61K 47/62* (2017.08); *A61P 35/00* (2018.01); *A61P 37/04* (2018.01); *C07K 14/005* (2013.01); *C07K 14/15* (2013.01); *C07K 16/18* (2013.01); *A61K 38/00* (2013.01); *A61K 2039/55516* (2013.01); *C07K 2317/10* (2013.01); *C07K 2319/00* (2013.01); *C12N 2740/10022* (2013.01); *C12N 2740/10033* (2013.01)

(58) Field of Classification Search
None
See application file for complete search history.

(56) References Cited

FOREIGN PATENT DOCUMENTS

| WO | WO 2004/087748 A1 | 10/2004 |
| WO | WO 2011/119484 A1 | 9/2011 |
| WO | WO 2013/026452 A1 | 2/2013 |

OTHER PUBLICATIONS

Giri et al. ("Amyloid Peptide-Induced Cytokine and Chemokine Expression in THP-1 Monocytes Is Blocked by Small Inhibitory RNA Duplexes for Early Growth Response-1 Messenger RNA," The Journal of Immunology, 2003, 170: 5281-5294) (Year: 2003).*
Methe et al. ("The psychrophilic lifestyle as revealed by genome sequence of Colwellia psychrerythraea 34H through genomic and proteomic analyses," Proceedings of the National Academy of Sciences of the United States of America (2005), 102(31), 10913-10918) (Year: 2005).*
CAS Accession No. 2005:781063 for Methe et al. ("The psychrophilic lifestyle as revealed by genome sequence of Colwellia psychrerythraea 34H through genomic and proteomic analyses," Proceedings of the National Academy of Sciences of the United States of America (2005), 102(31), 10913-10918) (Year: 2005).*
De Parseval, N., et al., "Characterization of the Three HERV-H Proviruses with an Open Envelope Reading Frame Encompassing the Immunosuppressive Domain and Evolutionary History in Primates," *Virology*, 2001, vol. 279(2), pp. 558-569.

* cited by examiner

*Primary Examiner* — Christina Bradley
(74) *Attorney, Agent, or Firm* — Womble Bond Dickinson (US) LLP

(57) ABSTRACT

The invention provides for novel immunostimulating peptides, peptide constructs and compositions. Further, the invention provides for methods of treatment utilising the peptides, peptide constructs and compositions.

Figure 1A:
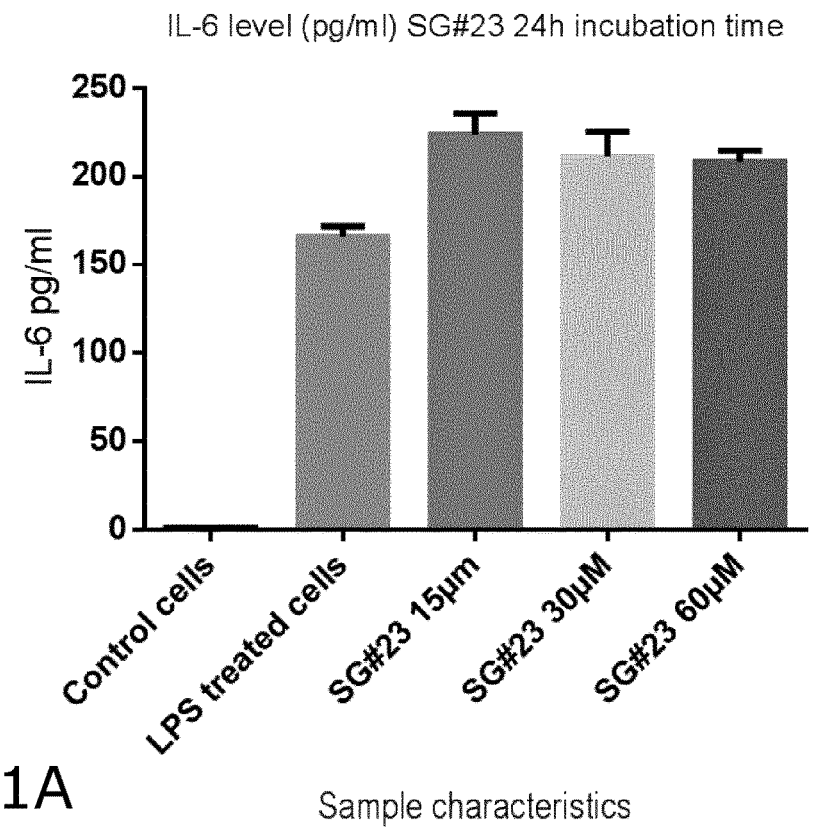
Figure 1B:
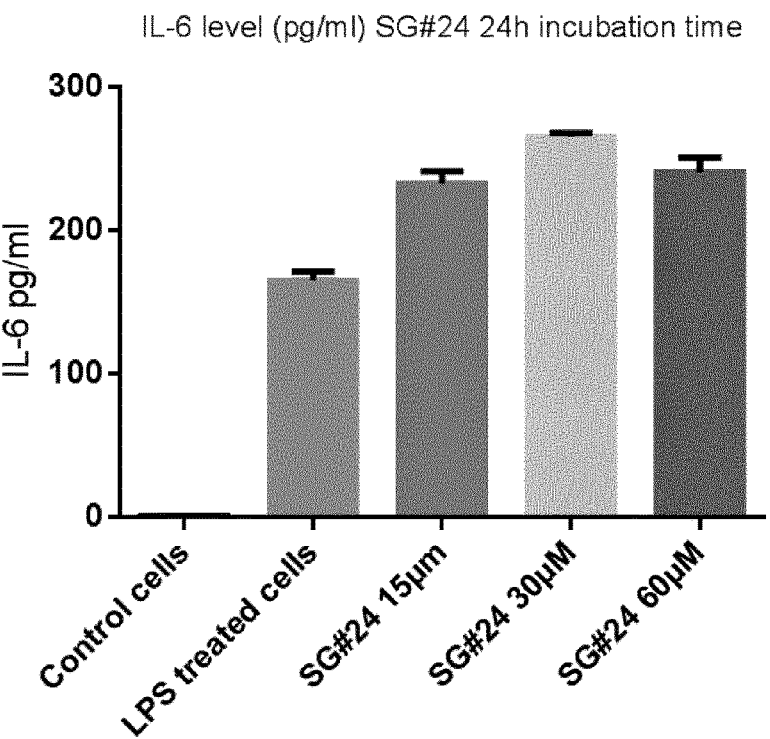
Figure 1C:
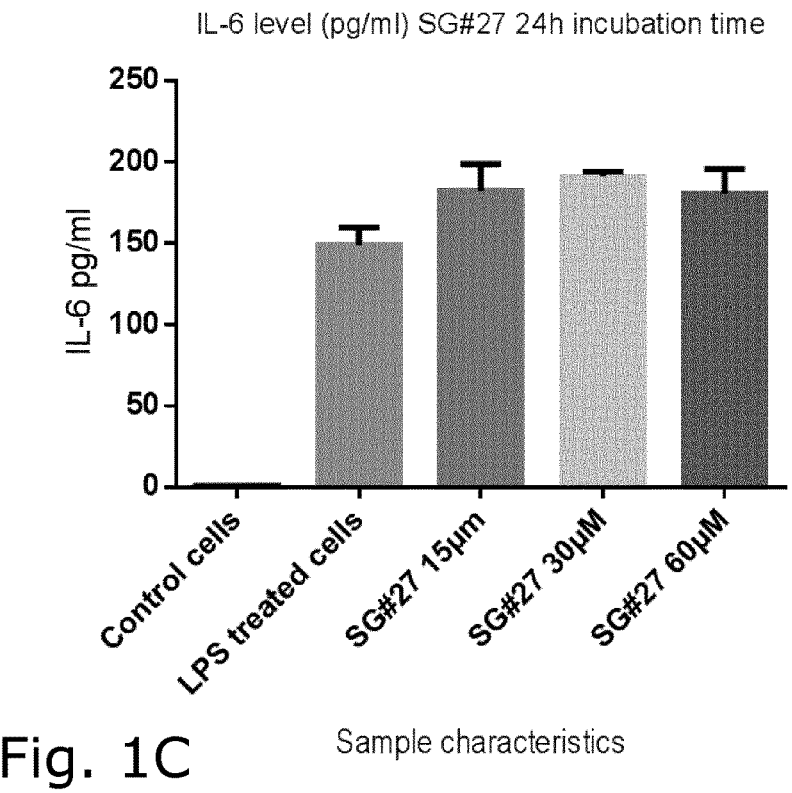
Figure 1D:
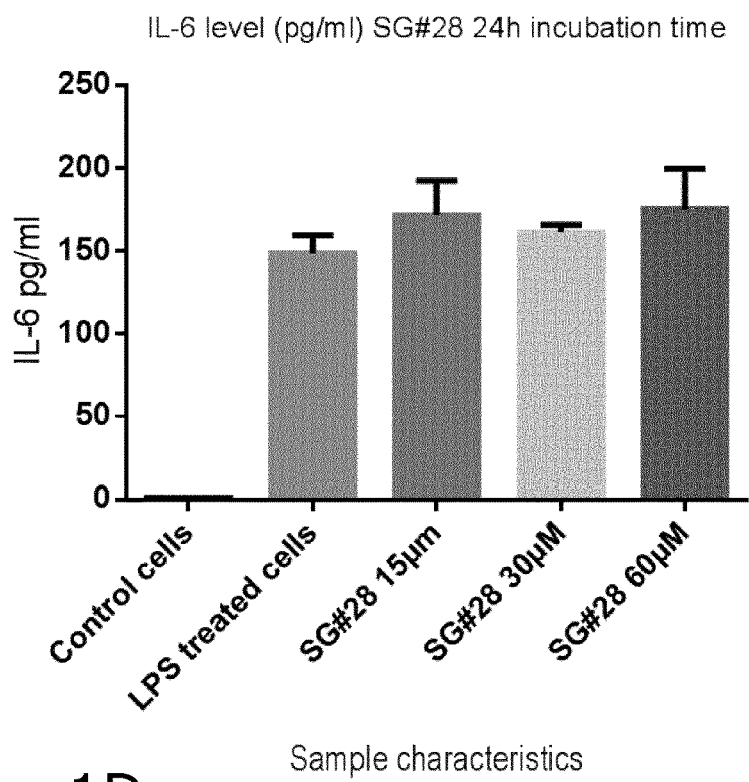
Figure 1E:
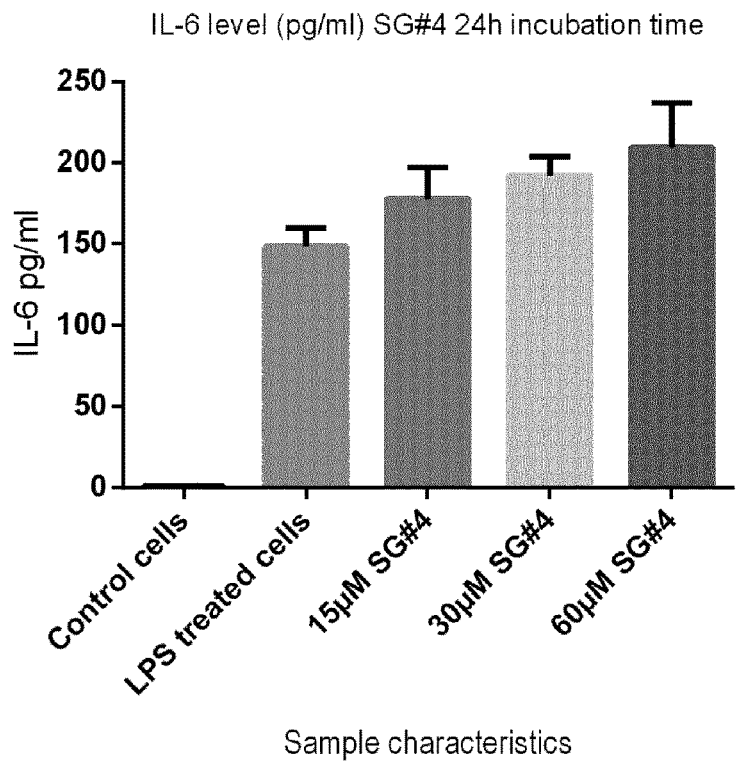

47 Claims, 10 Drawing Sheets
Specification includes a Sequence Listing.

TNF-alpha level (pg/ml) SG#4 24h incubation time (median LPS)

TNF-alpha level (pg/ml) SG#22 24h incubation time (median LPS)

TNF-alpha level (pg/ml) SG#23 24h incubation time (median LPS)

Sample characteristics

TNF-alpha level (pg/ml) SG#24 24h incubation time (median LPS)

Sample characteristics

IL-1 Betta level (pg/ml) SG#4 24h incubation time (median LPS)

IL-1 Betta level (pg/ml) SG#22 24h incubation time (median LPS)

IL-1 Betta level (pg/ml) SG#23 24h incubation time (median LPS)

Sample characteristics

IL-1 Betta level (pg/ml) SG#24 24h incubation time (median LPS)

Sample characteristics

IMMUNOSTIMULATING PEPTIDES

CROSS-REFERENCE TO RELATED APPLICATIONS

This application is a national stage filing under 35 U.S.C. 371 of PCT/EP2017/071228 filed Aug. 23, 2017, which International Application was published by the International Bureau in English on Mar. 1, 2018, and claims priority from Denmark Application No. PA 2016 70634, filed Aug. 23, 2016, International Application No. PCT/DK2016/050316, filed Sep. 30, 2016, and European Application No. 17165139.1, filed Apr. 5, 2017, which applications are hereby incorporated by reference in their entirety in this application.

FIELD OF THE INVENTION

The present invention relates to the field of therapy involving immune response modulation. In particular, the present invention relates to peptides, which exert an immune stimulatory effect as well as therapeutic applications of the peptides.

BACKGROUND OF THE INVENTION

Retroviruses are a group of viruses containing an RNA genome, which upon infection is reverse transcribed into a DNA copy, which IN TURN is integrated into the genome of the host cells. All progeny of such an infected cell will contain the viral genome (referred to as a pro-virus). All retroviruses include the three genes/coding sequences: gag, pol, and env.

The present invention primarily pertains to the env gene, the expression products thereof and in particular peptides derived from the ENV protein.

Human Endogenous Retro Viruses (HERVs) are ancient retroviral integrations permanently fixed in the genome of humans. The existence of functional proteins for most viral components of HERVs has been demonstrated, including the existence of the viral protease and the envelope surface protein. HERV derived proteins may have developed to exhibit a significant physiological potential and for example HERV derived envelope glycoproteins are abundantly expressed in placenta tissue and have been proposed to participate in syncytiotrophoblast differentiation by fusing the underlying cytotrophoblast cell layer.

Retroviral infections in general can cause significant immunosuppression as is known from HIV infections. Also, some human endogenous retroviruses show immune suppressive activity. More precisely, the envelope protein (env) of several retroviruses including HERVs are shown to have immune suppressive activity.

In the present applicant's pending international patent application PCT/DK2016/050316 (WO 2017/054831) is disclosed a number of peptides derived from HERV-H Env59 (also termed "Env 59"). These peptides were in particular demonstrated to be immunosuppressive and the peptides and variants thereof were tested for the ability to reduce secretion/expression of proinflammatory cytokines such as IL-6 from cells previously stimulated with LPS (lipopolysaccharide).

OBJECT OF THE INVENTION

It is an object of embodiments of the invention to provide novel immunostimulating agents useful in disease treatment and prevention. Further objects of embodiments of the invention are the provision of methods and compositions that utilise immunostimulating agents of the invention.

SUMMARY OF THE INVENTION

It has been found by the present inventor(s) that a subset of the Env 59-derived peptides and peptide constructs that were investigated in PCT/DK2016/050316 surprisingly exerted an immunostimulatory effect on LPS-stimulated PBMCs (peripheral blood mononuclear cells) and from LPS-stimulated THP-1 cells (cells of a human acute monocytic leukaemia cell line). This discovery opens for the possibility of providing novel immunostimulating agents that may be useful as immunologic adjuvants, general immune stimulators, vaccine adjuvants, or in immunotherapy protocols including effector molecules or as adjuvants in cancer immunotherapy protocols So, in a first aspect the present invention relates to a peptide comprising or consisting of a sequence variant of the amino acid sequence LQNRRGLGLSILLNEEC (SEQ ID NO: 1), wherein the sequence variant comprises at least one amino acid change compared to SEQ ID NO: 1, and wherein the peptide stimulates secretion and/or expression of cytokines when supplied in an effective concentration to THP-1 cells or PBMCs stimulated with lipopolysaccharide (LPS).

In a further aspect, the present invention relates to a peptide construct comprising a peptide of the invention and at least one further peptide, wherein the peptide and the at least one further peptide are either fused to each other or linked covalently via a side chain in at least one of the peptides in the peptide construct, wherein said further peptide is selected from the group consisting of
  an identical peptide according of the invention
  a non-identical peptide of the invention
  a fragment of at least 4 consecutive amino acid residues of a peptide of the invention, and
  the sequence $(GP)_n$, where n is a positive integer and preferably selected from 1, 2, 3, 4, 5, 6, 7, 8, 9, and 10.

In a third aspect, the present invention relates to a conjugate molecule, comprising a peptide or peptide construct of the invention, wherein said peptide or peptide construct is conjugated to a heterologous molecule, such as a heterologous peptide or polypeptide, a lipid, or a carbohydrate.

In a fourth aspect, the invention relates to a pharmaceutical composition comprising a peptide, a peptide construct, or a conjugate molecule of the invention, where said composition further comprises a pharmaceutically acceptable carrier, diluent or excipient.

In further aspects relating to therapy and/or prophylaxis, the invention relates to the peptides, peptide constructs, conjugate molecules and pharmaceutical compositions of the invention for various medical uses. These aspects also include methods of therapy and prophylaxis that employ the peptides, peptide constructs, conjugate molecules and pharmaceutical compositions of the invention.

Yet further aspects relate to nucleic acids encoding the peptides, peptide constructs, and conjugate molecules (where relevant), as well as compositions comprising these nucleic acids and the use of the nucleic acids in therapy and prophylaxis in a manner analogous to the uses and methods of the invention that utilise the peptides, peptide constructs and conjugate molecules as such.

Finally, an aspect of the invention also relates to a method of preparing antibodies targeting an immunogen, where the various agents of the present invention are used to enhance the immune response against an immunogen.

LEGENDS TO THE FIGURE

FIG. 1: Immunomodulatory function induced by peptide constructs on the expression/secretion levels of IL-6 protein secretion.

Figure 1F:
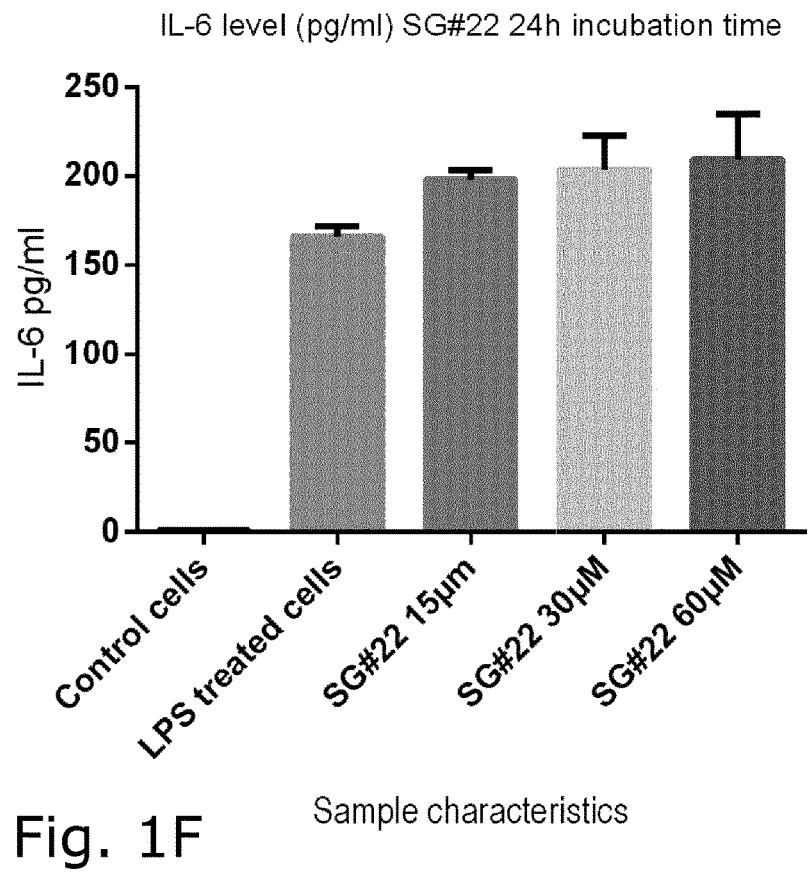

SG #23 (FIG. 1A), SG #24 (FIG. 1B), SG #27 (FIG. 1C), SG #28 (FIG. 1D), SG #4 (FIG. 1E), and SG #22 (FIG. 1F).

Figure 2:
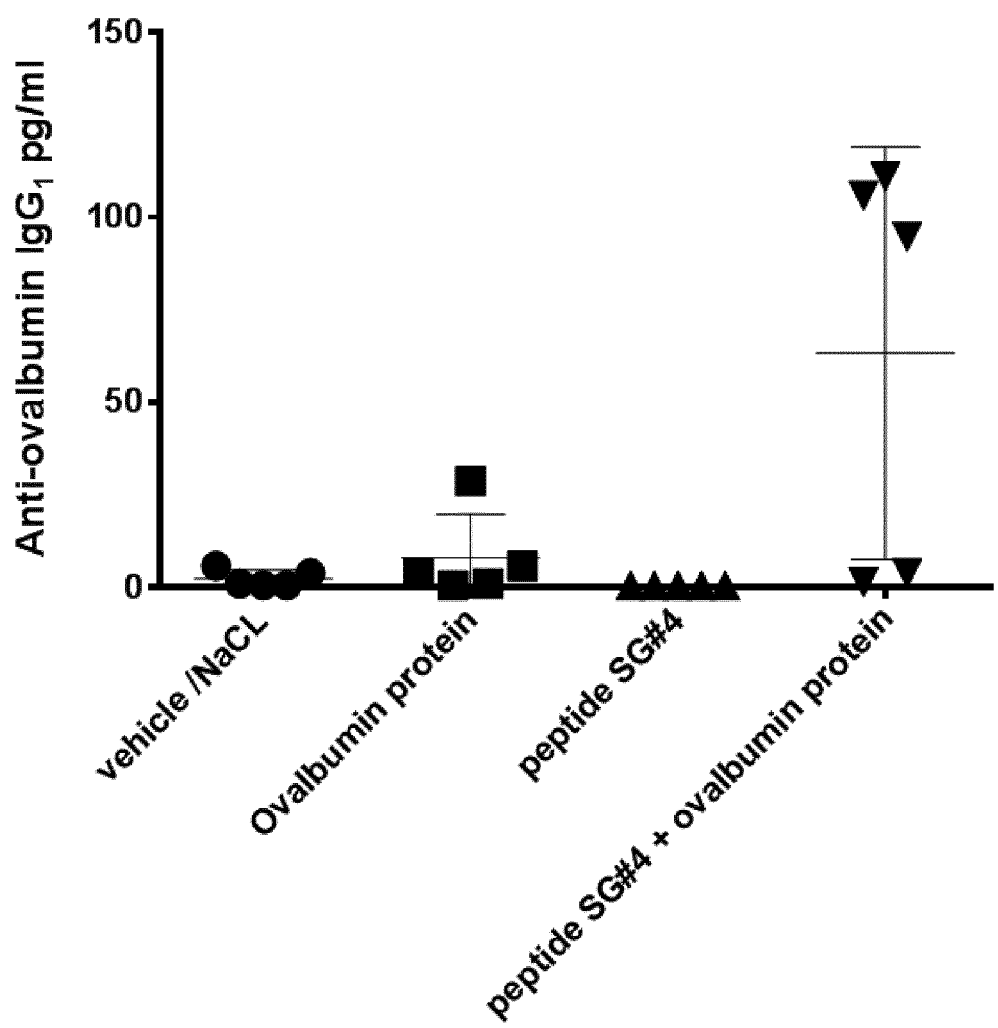

FIG. 2: Levels of anti-ovalbumin IgG$_1$ pg/ml in mice immunized with various compositions.

FIG. 3: Immunomodulatory function induced by peptide constructs on the expression/secretion levels of TNF-alpha protein secretion.

Figure 3A:
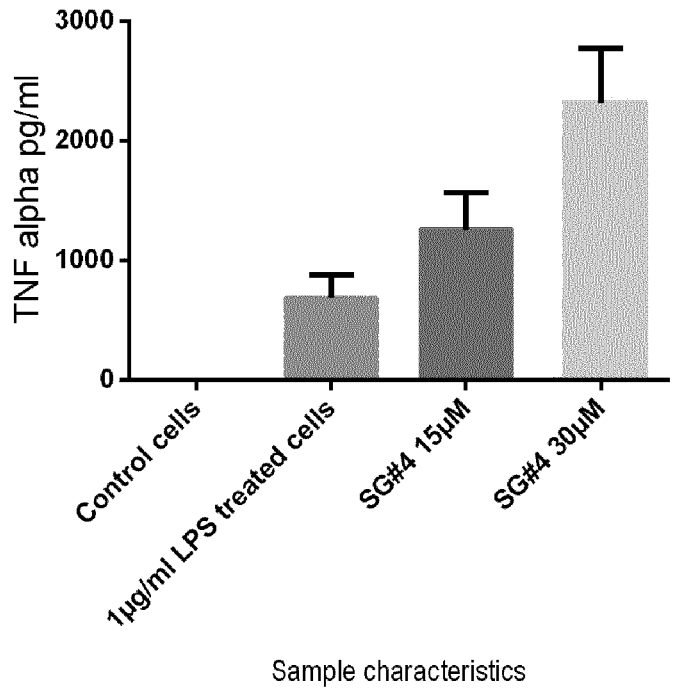
Figure 3B:
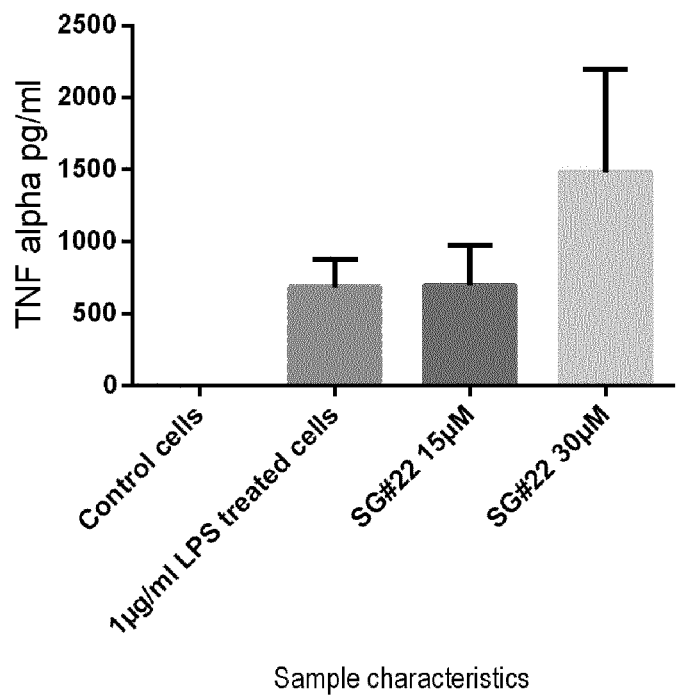
Figure 3C:
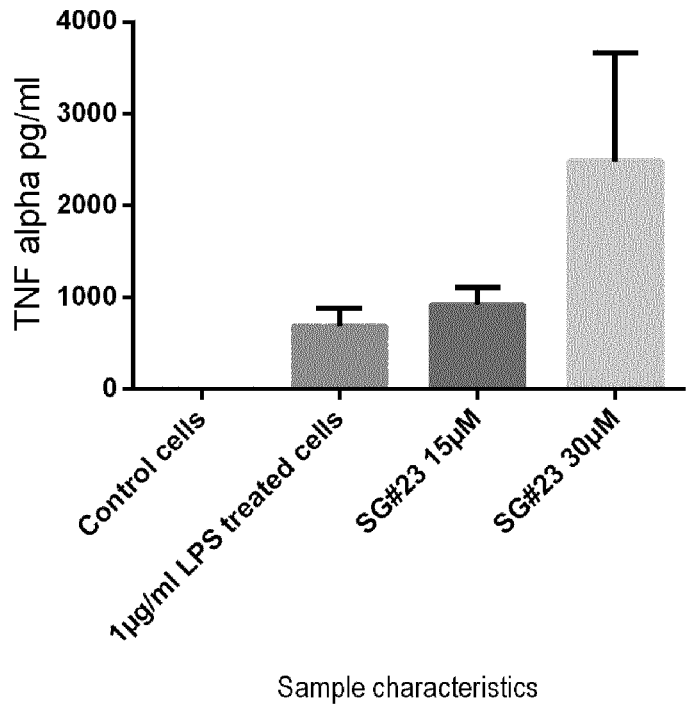
Figure 3D:
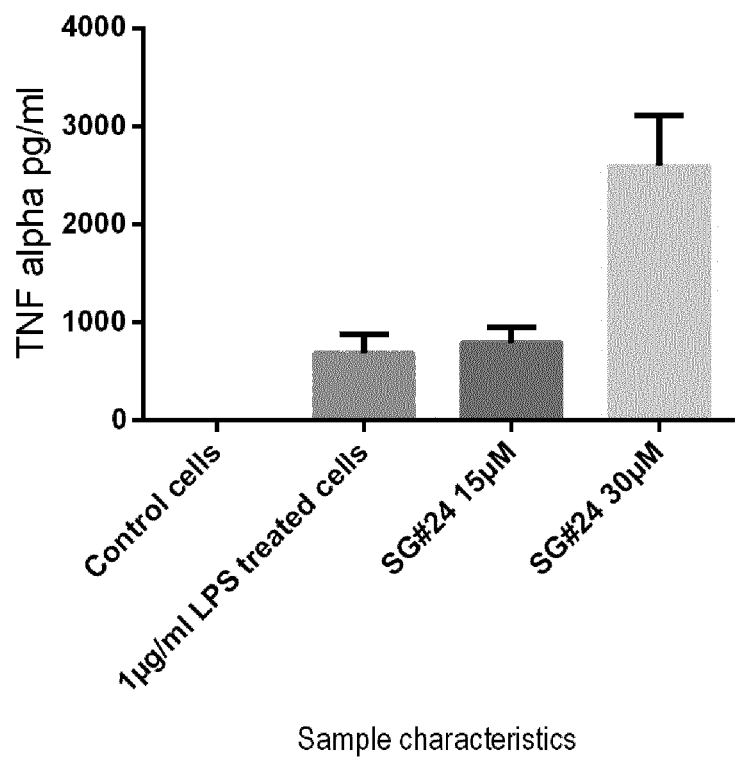
Figure 3E:
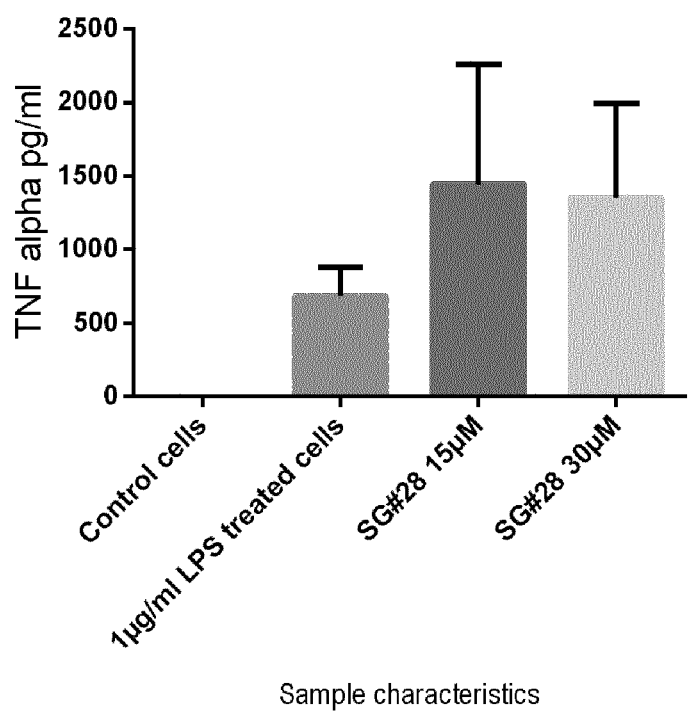
Figure 4A:
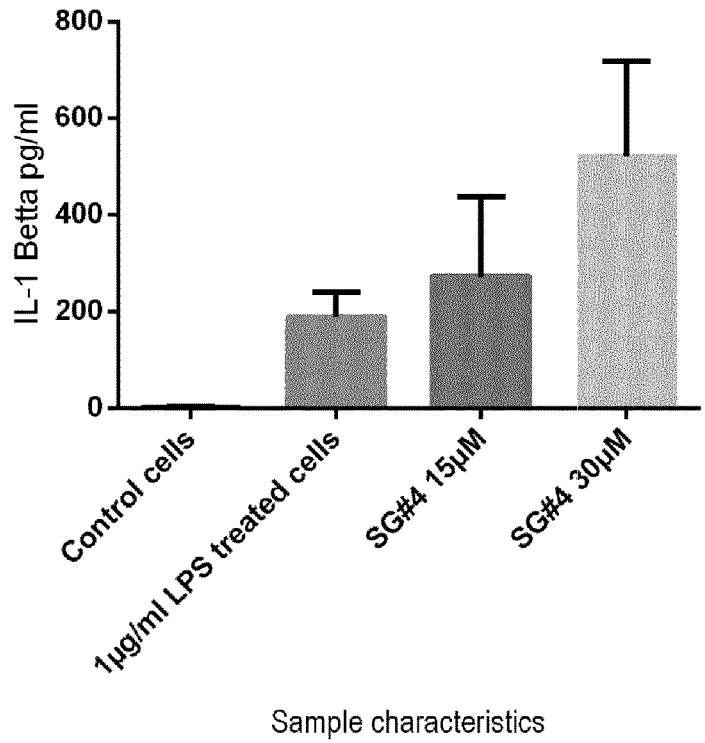
Figure 4B:
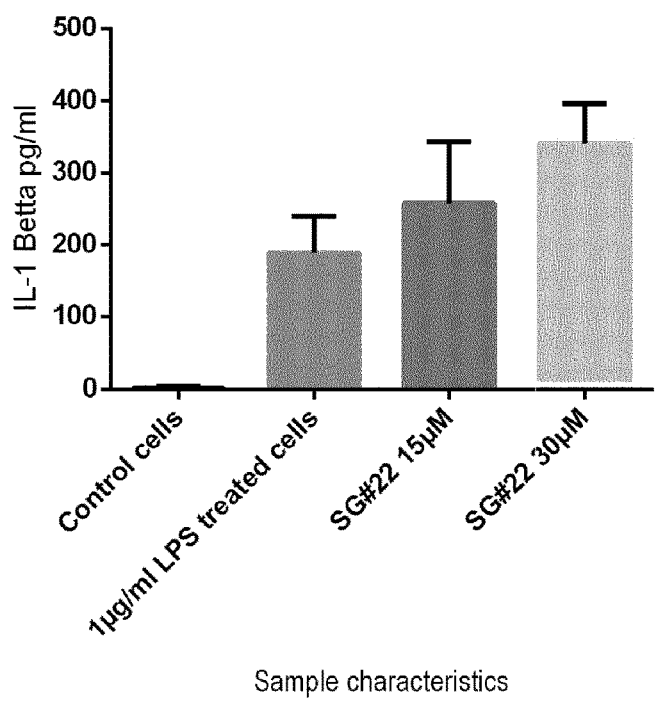
Figure 4C:
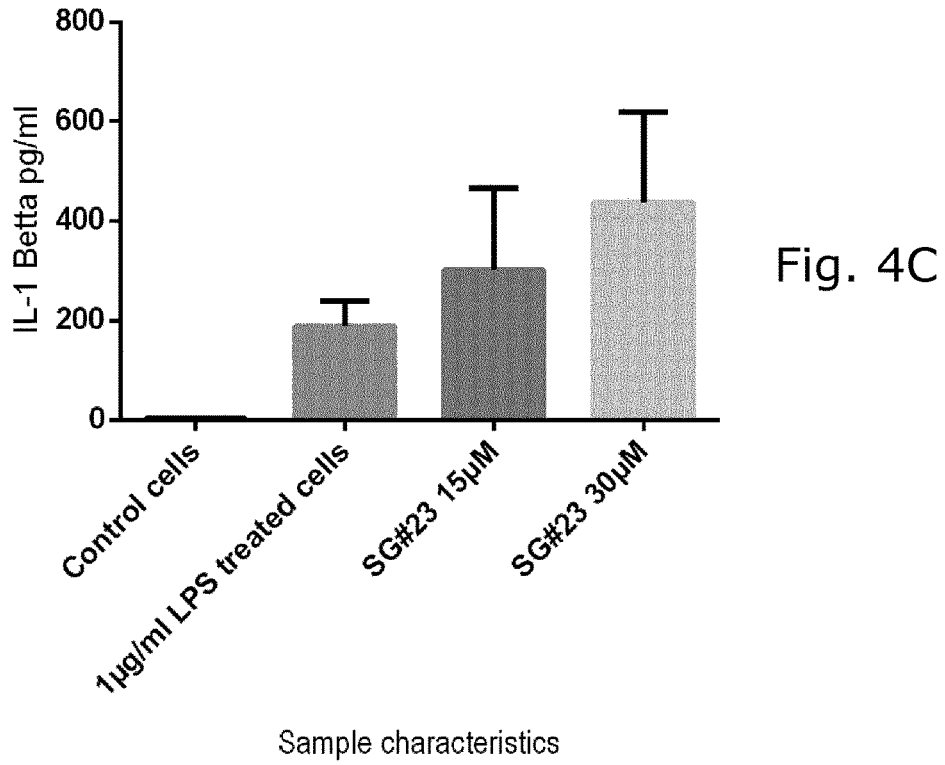
Figure 4D:
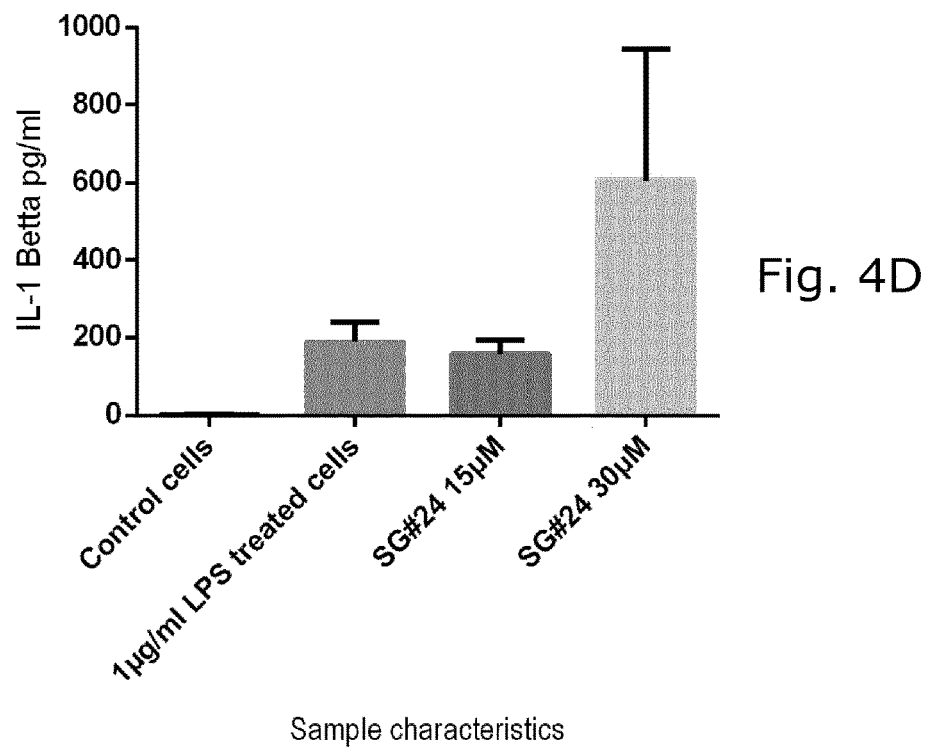
Figure 4E:
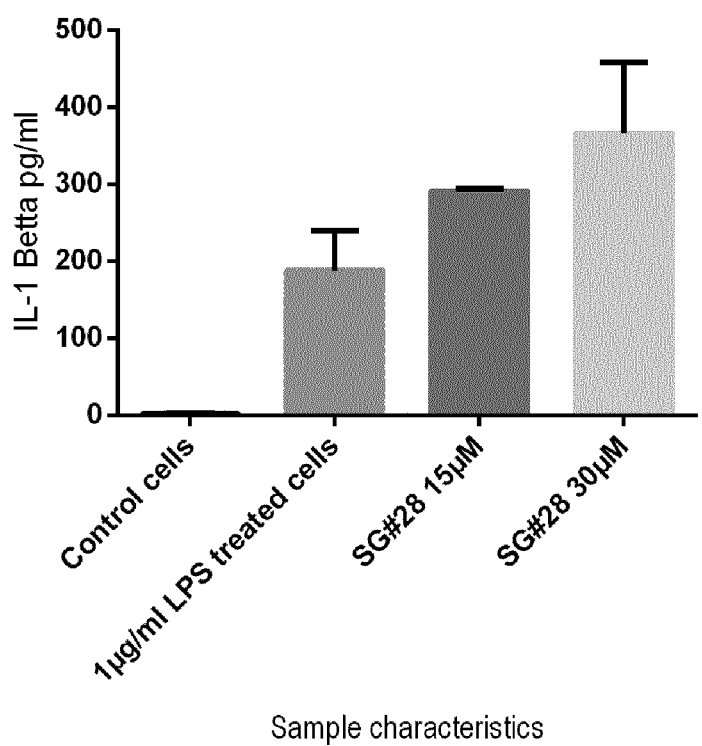

SG #4 (FIG. 3A), SG #22 (FIG. 3B), SG #23 (FIG. 3C), SG #24 (FIG. 3D), and SG #28 (FIG. 3E).

FIG. 4: Immunomodulatory function induced by peptide construct on the expression/secretion levels of IL-1 Beta protein secretion SG #4 (FIG. 4A), SG #22 (FIG. 4B), SG #23 (FIG. 4C), SG #24 (FIG. 4D), and SG #28 (FIG. 4E)

DETAILED DISCLOSURE OF THE INVENTION

Definitions

The following specific peptides/peptide constructs are referred to by sequence numbers herein:

| SEQ ID NO: | Amino acid sequence | Name of constructs including the sequences |
|---|---|---|
| 1 | LQNRRGLGLSILLNEEC | N/A[#] |
| 2 | LQNRRGLGLSILLNC | SG#4*, SG#27** |
| 3 | LQNKRGLGLSILLNEECGPGPGP | SG#8*, SG#28** |
| 4 | LQNRRGLGLSILLNEE | SG#13 |
| 5 | LQNRRGLGLSILLNEELQNRRGL | SG#14 |
| 6 | LQNKRGLGLSILLNC | SG#23* |
| 7 | LQNKKGLGLSILLNC | SG#24* |
| 8 | LQNXXGLGLSILLNXXX | Formula II[##] |
| 9 | GLSILLNEE | SG#22 |
| 10 | XXXXXXXGLSILLNXXX | Formula I[##] |

[#]Wild-type reference sequence from Env 59
*Peptides prepared as dimers of the peptides with the SEQ ID NOs, see below
**Peptides prepared as dimers of the peptides with the SEQ ID NOs, and peptides amidated in the C-terminus, see below
[##]Generic formula of certain peptides of the invention As used herein, the expression "a dimer" typically relates to either an end-to-end fusion peptide between 2 peptides of the invention or to any form of covalently linked dimers of two peptides, where the link involves a side chain in at least one of the 2 peptides. Hence, a dimer may be a "homodimer", which consists of two identical peptides of the invention as is the case for the dimers of SEQ ID NO: 2 and the dimers of SEQ ID NO: 3; these are according to the invention preferably dimerized via a disulphide bridge (i.e. a cystine group formed from the cysteines of the two monomers) as shown for the following preferred dimers of the invention:

```
SG#4:
LQNRRGLGLSILLNC (SEQ ID NO: 2)
              |
LQNRRGLGLSILLNC (SEQ ID NO: 2)

SG#8:
LQNKRGLGLSILLNEECGPGPGP (SEQ ID NO: 3)
                |
LQNKRGLGLSILLNEECGPGPGP (SEQ ID NO: 3)

SG#23:
LQNKRGLGLSILLNC (SEQ ID NO: 6)
              |
LQNKRGLGLSILLNC (SEQ ID NO: 6)
```

-continued

SG#24:
LQNKKGLGLSILLNC (SEQ ID NO: 7)
              |
LQNKKGLGLSILLNC (SEQ ID NO: 7)

SG#27:
LQNRRGLGLSILLNC-NH$_2$ (SEQ ID NO: 2, amidated C-terminus)
              |
LQNRRGLGLSILLNC-NH$_2$ (SEQ ID NO: 2, amidated C-terminus)

SG#28:
LQNKRGLGLSILLNEECGPGPGP-NH$_2$ (SEQ ID NO: 3, amidated C-terminus)
              |
LQNKRGLGLSILLNEECGPGPGP-NH$_2$ (SEQ ID NO: 3, amidated C-terminus)

Also, a dimer may be a heterodimer, i.e. a dimeric construct as described above, but composed of two non-identical peptides of the invention that are fused end-to-end or connected via a linker that involves a side chain in at least one of peptides in the heterodimer.

Covalent linking of dimers, trimers and multimers will typically be via a disulfide bridge when the monomers contain Cys residues, but alternatives are according to the invention available: For instance, a linker is typically selected from the group consisting of a glycine linker, a lysine linker, a glycine-lysine linker, a cysteine-lysine linker (typically established in the form of an amide bond between (2-oxo-ethyl) derivatized cysteine in one peptide and lysine in the other peptide), an Arg linker, and a bis-maleimide linker, but any linker for covalent coupling of peptide chains known in the art may be useful. Peptides of the invention, where no cysteine is present are thus typically intended for use as immunostimulating monomers or alternatively as dimers, trimers and multimers that are linked via other functional groups than the thiol groups of cysteines.

Other multimers than dimers are embodiments of the invention—these may be trimers or other multimers, such as homotrimers or homomultimers, but also heterotrimers and heteromultimers.

A "peptide" is in the present context a molecule constituted by a chain of peptide bonded amino acid residues.

A "peptide construct" is in the present context a molecule or complex comprised of two or more peptides of the invention. These may be linked end-to end (i.e. fused), but preferably the peptide constructs are coupled via a linker, such as a disulfide linker, cf. below for details.

A "conjugate molecule" is in the present context a peptide or peptide construct of the invention, which is further coupled to another heterologous molecule. For details pertaining to these further molecules, cf. below.

When using the term "non-modified" in the context of the present invention's peptide constructs, it is herein meant that the peptide discussed is monomeric and constituted by naturally occurring amino acid residues connected by peptide bonds only; in other words, an unmodified peptide (such as SG #13 and SG #22) does not include any N- or C-terminal modifications, and it is not linked to other peptides or chemical entities.

SPECIFIC EMBODIMENTS OF THE INVENTION

1$^{st}$ Aspect Peptides of the Invention

A peptide of the invention is based on the naturally occurring amino acid sequence SEQ ID NO: 1, that is, it is a sequence variant comprising at least one amino acid change compared to SEQ ID NO: 1, and wherein the peptide stimulates secretion and/or expression of cytokines when supplied in an effective concentration to THP-1 cells or PBMCs stimulated with lipopolysaccharide (LPS). As noted above, given the fact that the peptide having SEQ ID NO: 1 and molecules derived therefrom are generally immunosuppressive agents, it is highly surprising that the presently disclosed peptides exert an immunostimulating effect. In turn, this makes the presently disclosed peptides valuable as pharmaceutical compounds or adjuvants for use in clinical settings where stimulation of an immune response is warranted/desirable.

When stating that a peptide of the invention " . . . stimulates secretion and/or expression of cytokines when supplied . . . " is herein mean that the peptide has this stimulating effect either when it is supplied as an isolated molecule or when it is supplied to the THP-1 cells or PBMCs as part of a dimer or multimer of the invention. In other words, the isolated peptides disclosed herein may in some cases appear as incapable of exerting the immunostimulating function, e.g. when being part of a dimer, trimer or other multimer. This is e.g. the case for the peptide having SEQ ID NO: 9, which in its own right is immunostimulating as surprisingly demonstrated in the present application, but which is part of immunosuppressive constructs such as the following dimeric constructs, which are both disclosed in WO 2017/054831:

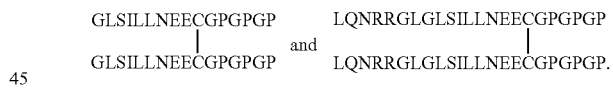

Other peptides, such as the peptide having SEQ ID NO: 4 which in its own right is immunostimulating but is also immunostimulating when present in the dimeric constructs SG #8 and SG #28.

In all embodiments of the peptide of the invention, it is possible and sometimes preferable that the C-terminal carboxyl group is modified, preferably by amidation (which i.a. provides for increased stability of the constructs of the invention and a change in charge in positive direction due to the removal of the C-terminal, negatively charged, carboxyl group in the peptide), but other modifications are possible, in particular those that render the charge of the peptide less negative or more positive. In general, it is believed that the net charge of an important subgroup of the peptides of the invention is more positive (higher) than that of the peptide having SEQ ID NO: 1, meaning that in peptides of the invention, the net charge of the peptide at neutral pH is preferably increased compared to the net charge of the peptide having the amino acid sequence SEQ ID NO: 1. However, as will be apparent from the present disclosure, the SG #22 peptide (with SEQ ID NO: 9) has a lower net charge than the reference peptide of SEQ ID NO: 1 but yet provides for a immunostimulatory effect.

The net charge of the peptide having SEQ ID NO: 1 is −0.1 at pH 7, where peptides and peptide constructs disclosed specifically herein have the following charges at pH 7:

| Peptide construct | Charge at pH = 7 |
|---|---|
| SG#4 | 4.0 |
| SG#8 | 0.0 |
| SG#13 | 0.0 |
| SG#14 | 2.0 |
| SG#22 | −2.0 |
| SG#23 | 4.0 |
| SG#24 | 4.0 |
| SG#27 | 5.8 |
| SG#28 | 1.8 |

So in important embodiments, the amino acid change(s) in SEQ ID NO: 1 are with amino acid residues that—when substituting positions in SEQ ID NO: 1—provides for a higher net charge at neutral pH. In particular, the preferred substituent in each position in SEQ ID NO: 1 is an amino acid residue which provides for a higher net charge than the substituted residue at neutral pH. As mentioned above, introduction of a C-terminal modification, which removes the negatively charged carboxyl group can add to this effect.

Another important feature of a number of the non-modified immunostimulating peptides of the invention is the absence of SEQ ID NO: 11 (CGPGPGP) and SEQ ID NO: 12 (GPGPGP), which are typically introduced to increase water solubility and which can be found in e.g. SEQ ID NO: 3 in the C-terminus. It has been found by the present inventor that certain non-modified peptides that do not include SEQ ID NO: 11/12 are immunostimulating, whereas corresponding dimeric peptides that include SEQ ID NO: 11 or 12 are immunosuppressive—the latter peptide constructs can typically be rendered immunostimulating by presenting them in monomeric form as disclosed herein.

The amino acid change(s) of the peptide of the invention is/are typically independently selected from substitution, deletion, and insertion.

Hence, in embodiments of the invention, the peptide comprises a sequence variant, which has 1, 2, or 3 amino acid change(s) in positions 15-17 of SEQ ID NO: 1. For example, the amino acid change is deletion of one or more of residues 15-17, such as deletion of one or both of residues 15 and 16, or deletion of residue 17.

Also, some of the peptides of the invention, including those discussed above are those, wherein the sequence variant comprises an amino acid change in position 4 of SEQ ID NO: 1. In important embodiments, the amino acid change of position 4 is a substitution. The substituting amino acid is preferably one which—together with the other changes relative to SEQ ID NO: 1—provides for an increase of the overall charge compared with the charge of SEQ ID NO: 1, so preferred substituents at position 4 are preferably positively charged like Arg. Other substituents would be certain non-proteinogenic amino acids, such as thialysine and canavanine. The preferred substituent at position 4 is a lysine residue.

Also, some of the peptides of the invention, including those discussed above are those, wherein the sequence variant comprises an amino acid change in position 5 of SEQ ID NO: 1.

In important embodiments, the amino acid change of position 5 is a substitution. The substituting amino acid is preferably one which—together with the other changes relative to SEQ ID NO: 1—in the provides for an increase of the overall charge compared with the charge of SEQ ID NO: 1, so preferred substituents at position 5 are preferably positively charged like Arginine. Other substituents would be certain non-proteinogenic amino acids, such as thialysine and canavanine. The preferred substituent at position 5 is a lysine residue. Also a number of the N-terminal amino acids may be deleted. For instance, amino acids 1-7 may be deleted in SEQ ID NO: 1, but also amino acids 1-6, 1-5, 1-4, 1-3, 1-2, or 1 may be deleted.

Preferred peptides of the invention have the formula I:

$$Z^1Z^2Z^3X^1X^1Z^4Z^5GLSILLNX^3X^4X^5 \quad (I)$$

wherein
$Z^1$ is L or absent,
$Z^2$ is Q or absent,
$Z^3$ is N or absent,
$Z^4$ is G or absent,
$Z^5$ is L or absent,
$X^1$ is R or K or absent,
$X^2$ is R or K or absent,
$X^3$ is E or absent,
$X^4$ is E or absent, and
$X^5$ is C or absent,
with the proviso that Formula I does not have the amino acid sequence SEQ ID NO: 1.

In some embodiments of the peptide of the invention, then in formula I:
if $Z^1$ is present then $Z^2$-$Z^5$, $X^1$, and $X^2$ are all present;
if $Z^2$ is present, then $Z^3$-$Z^5$, $X^1$, and $X^2$ are all present;
if $Z^3$ is present, then $Z^4$ and $Z^5$, $X^1$, and $X^2$ are all present;
if $Z^4$ is present, then $Z^5$, $X^1$, and $X^2$ are all present;
if $X^1$ is present, then $X^2$ is present.

In these embodiments of formula I, $Z^1$ may be absent, or $Z^2$ may be absent, or $Z^3$ may be absent, or $Z^4$ may be absent, or $Z^5$ may be absent, or $X^1$ may be absent, or $X^2$ may be absent. Also, in these embodiments, a subset of embodiment are those wherein $Z^1$ is present, or $Z^2$ is present, or $Z^3$ is present, or $Z^4$ is present, or $Z^5$ is present, or $X^1$ is present, or $X^2$ is present.

The peptide of the invention disclosed above is preferably one having formula I wherein $X^3$, $X^4$, and $X^5$ are all present, or only one of $X^3$ and $X^4$ is present and $X^5$ is present, or only $X^5$ is present, or none of $X^3$-$X^5$ is present. It will be understood that absence of $X^5$ renders the peptide unsuitable for dimerization via disulphide bridging, meaning that peptides lacking $X^5$ are either used in monomeric form or are used in dimers, trimers, or multimers, which rely on other functional groups than the thiol groups in cysteine.

Formula I is also provided as SEQ ID NO: 8 herein.

A subset of the peptides of formula I are defined by formula II:

$$LQNX^1X^2GLGLSILLNX^3X^4X^5 \quad (II)$$

wherein
$X^1$ is R or K,
$X^2$ is R or K,
$X^3$ is E or absent,
$X^4$ is E or absent, and
$X^5$ is C or absent,
with the proviso that Formula II does not have the amino acid sequence SEQ ID NO: 1.

The particularly preferred peptides of the present invention are those that have the amino acid sequences set forth in any one of SEQ ID NOs: 2-7, and 9.

Second Aspect—The Peptide Constructs of the Invention

The peptides of the invention are useful as immunostimulating agents in their own right, but some are also presented as dimers and other multimers, i.e. as peptide constructs of the invention comprising a peptide of the first aspect of the invention and at least one further peptide, wherein the peptide and the at least one further peptide are either fused to each other or (preferably) linked covalently via a side chain in at least one of the peptides in the peptide construct, wherein said further peptide is selected from the group consisting of an identical peptide of the first aspect of the invention,
a non-identical peptide of the first aspect of the invention,
a fragment of at least 4 consecutive amino acid residues of a peptide of the first aspect of the invention, and
the amino acid sequence $(GP)_n$, where n is a positive integer and preferably selected from 1, 2, 3, 4, 5, 6, 7, 8, 9, and 10; this latter second peptide is typically fused to the N- or C-terminus of a peptide of the first aspect of the invention and may be used in isolation as a fusion partner or as a fusion partner to a peptide of the first aspect of the invention, which in turn is part of a dimer, trimer or other multimer; cf. e.g. the constructs SG #8 and SG #28.

Surprisingly, non-modified peptides that in their own right are immunostimulating can preserve their immunostimulating effect when presenting them in the form of dimers, trimers, and other multimers (or by including the above described modifications); this is highly surprising in view of the fact that the vast majority of the dimers presented in WO 2017/054831 are immunosuppressive.

The peptide construct is thus typically in the form of a multimer, such as a homodimer or heterodimer of peptide(s) of the first aspect of the invention. The peptide and the at least one further peptide are for instance linked covalently via a side chain in at least one of the peptides in the peptide construct, where the link is selected from the group consisting of a disulphide bridge, a glycine linker, a lysine linker, a glycine-lysine linker, a cysteine-lysine linker, an Arg linker, and a bis-maleimide linker, cf. the discussion above. It is preferred to utilise disulphide binding where the peptides forming the construct sol allow.

If the covalent link does not involve side chains in all peptides of the multimer, the coupling between peptides will either be a traditional end-to-end fusion, or it may be a coupling between a side chain and a terminus of the backbone of one of the other peptides.

Third Aspect—Conjugate Molecules of the Invention

The peptides and peptide constructs of the invention find use as immunostimulatory agents, either alone or combined in compositions with other therapeutically active substances. It is however an important aspect of the invention that the peptides and peptide constructs may form part of conjugates with other molecules; in case these other molecules are peptides, polypeptides or proteins, one convenient conjugation type is fusion via peptide bonds, but other molecules such as carbohydrates and lipids will require other types of conjugation.

The peptide or peptide construct is in this aspect therefore conjugated to or internally in for instance a heterologous molecule, such as a heterologous peptide or polypeptide, a lipid, or a carbohydrate, but any molecular entity may be used for conjugation/fusion; for instance, the molecules that could form other parts of the compositions discussed below are believed to be useful conjugation partners also.

When a conjugate molecule comprises a peptides or peptide construct of the invention as part of a fusion construct the peptides and peptide construct can be placed as an N- or C-terminal fusion partner or inserted internally in a larger (poly)peptide, which means that the peptide or peptide construct of the invention has both a C- and N-terminal fusion partner. Typical lengths of such fusion constructs are about 20, 30, 40, 50, 60, 70, 80, 90, or 100 amino acid residues.

In case a conjugate molecule comprises a heterologous (poly)peptide, this may according to the invention comprise a C-terminal amidation. In general, a conjugate molecule can according to the invention be C-terminally amidated.

The term "heterologous molecule" in the present context denotes a molecule to which the peptide or peptide construct has to be chemically attached or by recombinant technology or by means synthetic chemistry, because no natural association exists. "Attached" also includes that the peptide or peptide construct may be introduced into a heterologous molecule such as a protein.

The heterologous molecule of the conjugate molecule is typically selected from the group consisting of a hormone or active fragment thereof, a cytokine or active fragment thereof, an immunogenic protein or peptide, an immunologic carrier, an immunotherapeutic drug, a cancer chemotherapy drug, a chemotactic agent, an antibody or specifically binding fragment thereof, a ligand for a receptor, a receptor or ligand binding fragment thereof, and a TCR-binding peptide. "Active fragments" are fragments of a biologically active molecule that retains a biologic activity that characterises the full-size molecule from which the fragment is derived. An active fragment of a cytokine hence e.g. preserves an appreciable amount of cytokine activity. The heterologous molecule can also be a immunogenic carrier, such as those immunogenic carrier proteins that are typically used in vaccine technology, e.g. tetanus toxoid, diphtheria toxoid, and KLH, and immunogenic fragments thereof.

If the conjugate molecule is provided by means of chemical conjugation between a peptide or peptide construct of the invention and a heterologous molecule (i.e. conjugation not via a peptide bond), then conjugation may be via a linker as detailed above in connection with the second aspect, or the chemical conjugation is conjugation using a cross-linking agent such as formaldehyde or glutaraldehyde.

Fourth Aspect—Pharmaceutical Compositions of the Invention

Important uses of the above-detailed agents are as part of a pharmaceutical composition comprising a peptide, a peptide construct, or a conjugate molecule of the invention where said composition further comprises a pharmaceutically acceptable carrier, diluent or excipient. In addition, the pharmaceutical composition may comprise an active ingredient selected from the group consisting of an immunogen, an antigen, an antibody, an antibody fragment, an antibody analogue, a monoclonal antibody, a chemotherapeutic agent, an immune stimulating compound, a hormone, and an immune checkpoint inhibitor.

For instance, the further active ingredient of the pharmaceutical composition can be a chemotherapeutic agent selected from the group consisting of an alkylating agent, preferably selected from the group consisting of a bifunctional alkylating agent, such as cyclophosphamide, mechlorethamine. chlorambucil, and melphalan, and a monofunctional alkylating agent, such as dacarbazine (dtic), a nitrosourea compound, and temozolomide (oral dacarbazine);

an anthracycline, preferably selected from the group consisting of daunorubicin, doxorubicin, epirubicin, idarubicin, mitoxantrone, and valrubicin;

a cytoskeletal disruptor (taxane), preferably selected from the group consisting of paclitaxel, docetaxel, abraxane, and taxotere;

an epothilone, preferably selected from the group consisting of epothilone b, patupilone, sagopilone, ixabepilone, and utidelone;

a histone deacytelase inhibitor, preferably selected from the group consisting of vorinostat and romidepsin;

a topoisomerase I inhibitor, preferably selected from the group consisting of irinotecan and topotecan;

a topoisomerase II inhibitor, preferably selected from the group consisting of etoposide, teniposide, and taflupo side;

a kinase inhibitor, preferably selected from the group consisting of bortezomib, erlotinib, gefitinib, imatinib, vemurafenib, and vismodegib, a nucleotide or precursor analogue, preferably selected from the group consisting of azacitidine, azathioprine, capecitabine, cytarabine, doxifluridine, fluorouracil, gemcitabine, hydroxyurea, mercaptopurine, methotrexate, and tioguanine;

a peptide antibiotic, preferably selected from the group consisting of bleomycin and actinomycin;

a platinum-based agent, preferably selected from the group consisting of carboplatin, cisplatin, and oxaliplatin;

a retinoid, preferably selected from the group consisting of tretinoin, alitretinoin, and bexarotene; and a vinca alkaloid, preferably selected from the group consisting of vinblastine, vincristine, vindesine, and vinorelbine.

Also, the further active ingredient of the pharmaceutical composition can be a immunotherapeutic agent selected from the group consisting of a PD-1 inhibitor, preferably selected from pembrolizumab and nivolumab;

a PD-L1 inhibitor, preferably selected from atezolizumab and avelumab; and an anti CTLA-4 compound, preferably ipilimumab.

The pharmaceutical composition of the invention may be a vaccine, e.g. a product for use in conducting active specific immunotherapy, but also other formulations are A pharmaceutical composition comprises in addition to the agents discussed above therapeutically inactive ingredients, such as a pharmaceutically acceptable or physiologically acceptable excipient, carrier and/or adjuvants, which are well-known to the person skilled in the art and may include, but are not limited to, solvents, emulsifiers, wetting agents, plasticizers, solubilizers (e.g. solubility enhancing agents) coloring substances, fillers, preservatives, anti-oxidants, anti-microbial agents, viscosity adjusting agents, buffering agents, pH adjusting agents, isotonicity adjusting agents, mucoadhesive substances, and the like.

In some embodiments, the peptide, peptide construct or conjugate molecule may be formulated (e.g. mixed together) with further immune-modifying agents like adjuvants—this is particularly relevant when used as a vaccine ingredient. The (further) adjuvant may be any conventional adjuvant, including but not limited to oxygen-containing metal salts, e.g. aluminum hydroxide, chitosan, heat-labile enterotoxin (LT), cholera toxin (CT), cholera toxin B subunit (CTB), polymerized liposomes, mutant toxins, e.g. LTK63 and LTR72, microcapsules, interleukins (e.g. IL-1 BETA, IL-2, IL-7, IL-12, INFGAMMA), GM-CSF, MDF derivatives, CpG oligonucleotides, LPS, MPL, MPL-derivatives, phosphazenes, Adju-Phos®, glucan, antigen formulation, liposomes, DDE, DHEA, DMPC, DMPG, DOC/Alum Complex, Freund's incomplete adjuvant, ISCOMs®, LT Oral Adjuvant, muramyl dipeptide, monophosphoryl lipid A, muramyl peptide, and phospatidylethanolamine. Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M.

In some embodiments, the pharmaceutical composition may be formulated for parenteral administration, such as formulated for injection, e.g. subcutaneous and/or intradermal injection. Therefore, in some embodiments, the pharmaceutical composition may be a liquid (i.e. formulated as a liquid), including a solution, a suspension, a dispersion, and a gelled liquid. For example, a liquid pharmaceutical composition may be formed by dissolving a powder, granulate or lyophilizate of a peptide, peptide construct or conjugate molecule described herein in a suitable solvent and then administering to a subject. Suitable solvents may be any solvent having physiologically acceptable properties and able to dissolve the peptide combination in desired concentrations. A desired concentration may depend on the aliquot to be administered (i.e. to be injected) and the desired single dose. It is emphasized that for the purposes of injection the aliquot is in the range of about 10 to 500 microliters, e.g. 50 to 300 microliters or less and a desired single dose is within range of 1 to 1000 nanomole. Therefore, a suitable solvent should be able to dissolve any peptide of the combination to achieve a final concentration of about 1 to 1000 µM for peptide, peptide construct or conjugate molecule. Thus, in one embodiment, a liquid composition comprises the peptide, peptide construct or conjugate molecule in a concentration of 10 to 800 µM, for example 20 to 500 µM or 20 to 300 µM. Typically, the solvent is an aqueous solution, optionally mixed with other solvents. Thus, a solvent may comprise at least 60% w/w of water, e.g. at least 65% w/w, 70% w/w, 75% w/w, 80% w/w, 85% w/w, 90% w/w or 95% w/w, 99% w/w of water, such as distilled water, such as sterile water. In some embodiments, the solvent is sterile distilled water, e.g. water for injection. An aqueous solution may comprise other solvents than water, for example DMSO (dimethylsulfoxide), glycerol, ethanol, acetonitrile, vegetable or synthetic oils. The pH of the aqueous phase of the solvent may be in a physiological acceptable range, typically in the range of 3 to 9, such as in the range of pH 3 to 8, such as in the range of pH 4 to 8, such as in the range of 5 to 8, such as in the range of 6 to 8. Thus, the liquid formulation may comprise a pH controlling agent or buffering agent (e.g. citrate buffer, phosphate buffer, acetate buffer), optionally the pH may be adjusted with dilutions of strong base (e.g. sodium hydroxide or the like) and/or dilutions of strong acids (e.g. hydrochloric acid).

Typically, the liquid formulation is isotonic, and optionally sterile. Therefore, in some embodiments, the formulation comprises saline, such as isotonic saline. The liquid may contain additional excipients, such as another solvent, a solubilizing enhancing agent (e.g. polyoxyethylene (20) sorbitan monolaurate (Tween® 20), ionic and non-ionic emulsifiers (e.g. poloxamers (Kolliphor®)), a dispersant, a thickener, a preservative, an anti-microbial agent, and/or an antioxidant. Non-limiting illustrative examples of solvents include water, saline, DMSO, glycerol, ethanol, acetonitrile, vegetable or synthetic oils.

Some peptides are known to be prone to oxidation or being unstable when exposed to water for a long period. Therefore, to achieve storage stable compositions, a pharmaceutical composition may be formulated to contain only a limited amount of water or aqueous solution, e.g. containing less than 10% w/w of water or aqueous solution, such as less than 9, 8, 7, 6, 5, 4, 3, 2, 1, 0.5% w/w of water or aqueous solution. Examples of pharmaceutical compositions with limited levels of water may include granulates, powders, for example lyophilizates, i.e. freeze-dried powders. Typically, the freeze-dried composition may be dissolved before use, for example dissolved in an aqueous, optionally sterile, solution, for example a solution having a pH in the range of 3-9, such as pH in the range of 3 to 8, such as pH in the range of 4 to 8. A lyophilizate may contain additional ingredients, e.g. bulking agents and lyoprotectants (e.g. sucrose, lactose, trehalose, mannose, mannitol, sorbitol, glucose, raffinose, glycine, histidine or mixtures thereof), buffering agents (e.g. sodium citrate, sodium phosphate, disodium phosphate, sodium hydroxide, Tris base, Tris acetate, Tris HCl or mixtures thereof), antioxidants, antimicrobial agents, solubilizers (e.g. polyoxyethylene (20) sorbitan monolaurate (Tween® 20)).

A freeze-dried composition may also be formulated into a solid dosage form that is administered for example by the oral route such as by oral mucosa. Thus, in some embodiments, the pharmaceutical composition may be formulated for oral administration, for example for sublingual administration. Therefore, the pharmaceutical composition may be a solid dosage form, such as a freeze-dried solid dosage form, typically a tablet, a capsule or sachet, which optionally may be formulated for fast disintegration. Pharmaceutical formulations and delivery systems appropriate for the compositions, methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel ad Soklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

As mentioned, pharmaceutical compositions can be formulated to be compatible with a particular route of administration. Thus, pharmaceutical compositions may include carriers, diluents, or excipients suitable for administration by various routes. Exemplary routes of administration for contact or in vivo delivery for which a composition can optionally be formulated include inhalation, intranasal, oral, buccal, sublingual, subcutaneous, intradermal, epicutaneous, rectal, transdermal, or intralymphatic.

For oral, buccal or sublingual administration, a composition may take the form of, for example, tablets or capsules, optionally formulated as fast-integrating tablets/capsules or slow-release tablets/capsules. In some embodiments, the tablet is freeze-dried, optionally a fast-disintegrating tablet or capsule suitable for being administered under the tongue.

The pharmaceutical composition may also be formulated into a "unit dosage form", which used herein refers to physically discrete units, wherein each unit contains a predetermined quantity of the peptide, peptide construct or conjugate molecule, optionally in association with a pharmaceutical carrier (excipient, diluent, vehicle or filling agent) which, when administered in one or more doses, may produce a desired effect. Unit dosage forms also include, for example, ampules and vials, which may include a composition in a freeze-dried or lyophilized state (a lyophilizate) or a sterile liquid carrier, for example that can be added prior to administration or delivery in vivo. Unit dosage forms additionally include, for example, ampules and vials with liquid compositions disposed therein.

Peptides may be prone to degradation when exposed to oxygen, for example when exposed to air or solvents containing air. Therefore, in some embodiments, the pharmaceutical composition comprises an inert gas, e.g. argon or nitrogen.

Therapeutic Aspects

The peptide, peptide construct, conjugate molecule, or pharmaceutical composition of the invention finds use in therapy.

Due to their immunostimulating effects, the peptide, peptide construct, conjugate molecule, or pharmaceutical composition of the invention may be used "as is" in therapeutic or prophylactic settings in order to stimulate the immune system. So in situations, where the Ø

The peptide, peptide construct, conjugate molecule or pharmaceutical composition may according to the invention find use is a prophylactic or therapeutic treatment method for enhancing, stimulating or eliciting a specific adaptive immune response against an immunogen in a subject, where the method comprises co-administering a prophylactically or therapeutically active amount of said peptide, peptide construct, conjugate molecule or pharmaceutical composition and said immunogen to the subject in need of said prophylactic or therapeutic treatment.

The term "co-administration" denotes either simultaneous administration of the peptide/peptide construct/conjugate molecule/composition of the invention and a further active ingredient as part of the same administration (e.g. in the same composition) or as several separate administration (possibly at different times), where, however, the immunostimulatory effect of the peptide/peptide construct/conjugate molecule/composition of the invention is capable of enhancing the effect of the further active ingredient, in this case increasing the immune response against the immunogen. In other words, it is preferred that the peptide, peptide construct, conjugate molecule acts as an immunologic adjuvant, preferably in a vaccine.

The peptide, peptide construct, conjugate molecule or pharmaceutical composition also finds use in chemotherapeutic or an immunotherapeutic treatment of cancer in a subject, where the method comprises co-administering a therapeutically effective amount of said peptide, peptide construct, conjugate molecule or pharmaceutical composition and a chemotherapeutic and/or immunotherapeutic agent to the subject in need of said prophylactic or therapeutic treatment.

The chemotherapeutic agent is typically selected from the group consisting of
- an alkylating agent, preferably selected from the group consisting of a bifunctional alkylating agent, such as cyclophosphamide, mechlorethamine. chlorambucil, and melphalan, and a monofunctional alkylating agent, such as dacarbazine (dtic), a nitrosourea compound, and temozolomide (oral dacarbazine);
- an anthracycline, preferably selected from the group consisting of daunorubicin, doxorubicin, epirubicin, idarubicin, mitoxantrone, and valrubicin;

a cytoskeletal disruptor (taxane), preferably selected from the group consisting of paclitaxel, docetaxel, abraxane, and taxotere;

an epothilone, preferably selected from the group consisting of epothilone b, patupilone, sagopilone, ixabepilone, and utidelone;

a histone deacytelase inhibitor, preferably selected from the group consisting of vorinostat and romidepsin;

a topoisomerase I inhibitor, preferably selected from the group consisting of irinotecan and topotecan;

a topoisomerase II inhibitor, preferably selected from the group consisting of etoposide, teniposide, and tafluposide;

a kinase inhibitor, preferably selected from the group consisting of bortezomib, erlotinib, gefitinib, imatinib, vemurafenib, and vismodegib, a nucleotide or precursor analogue, preferably selected from the group consisting of azacitidine, azathioprine, capecitabine, cytarabine, doxifluridine, fluorouracil, gemcitabine, hydroxyurea, mercaptopurine, methotrexate, and tioguanine;

a peptide antibiotic, preferably selected from the group consisting of bleomycin and actinomycin;

a platinum-based agent, preferably selected from the group consisting of carboplatin, cisplatin, and oxaliplatin;

a retinoid, preferably selected from the group consisting of tretinoin, alitretinoin, and bexarotene; and a vinca alkaloid, preferably selected from the group consisting of vinblastine, vincristine, vindesine, and vinorelbine, and the immunotherapeutic agent is typically selected from the group consisting of a PD-1 inhibitor, preferably selected from pembrolizumab and nivolumab;

a PD-L1 inhibitor, preferably selected from atezolizumab and avelumab; and an anti CTLA-4 compound, preferably ipilimumab.

The peptide, peptide construct, conjugate molecule or pharmaceutical composition of the invention is further useful in a prophylactic or therapeutic treatment method for enhancing, stimulating or eliciting an immune response (e.g. an innate immune response) in a subject, where the method comprises administering said peptide, peptide construct, conjugate molecule or pharmaceutical composition to the subject in need of said prophylactic or therapeutic treatment. In this embodiment, the peptide, peptide construct, conjugate molecule or pharmaceutical composition thus acts as a separate pharmaceutical agent.

Also, the peptide, peptide construct, conjugate molecule or pharmaceutical composition of the invention finds use in therapeutic antibiotic treatment methods for treatment of infection with a virus, bacterium, fungus, or single cell parasite, or multicellular parasite, where the method comprises co-administering said peptide, peptide construct, conjugate molecule or pharmaceutical composition and said antibiotic to the subject in need of said therapeutic treatment. Any antibiotic treatment can benefit from the increased immunological awareness induced by the peptide, peptide construct, conjugate molecule or pharmaceutical composition of the present invention, meaning that combination treatment with any available antibiotic drug (penicillins, cephalosporins, chloramphenicol, tetracyclines, aminoglycosides, polymyxins, antimycobacterial drugs, sulphonamides, trimethoprim, antifungal agents, and antiviral agents).

With respect to dosage regimens and exact administered amounts of the peptide, peptide construct, conjugate molecule or composition of the invention, these will be determined readily by a skilled person depending on the exact condition treated and the age, gender, bodyweight, and general condition of the subject to be treated. It will be understood from the present disclosure that it is preferred to treat human subjects, but the present invention also finds use in veterinary medicine.

Aspect Relating to Antibody Production

Since the peptide, peptide conjugate, and conjugate molecule find use as immunological adjuvants, they find use in preparation of antibodies that specifically binds an immunogen. Such a method includes co-administration to an animal of an immunogenically active amount of a peptide, a peptide construct, a conjugate molecule, or a (pharmaceutical) composition disclosed herein, and the immunogen, so as to effect production of antibodies specific for said immunogen in said animal, and subsequently recovering said antibodies from the animal.

Co-administration is accomplished by administering the peptide, the peptide construct, the conjugate molecule, or the pharmaceutical composition, and the immunogen either as part of one pharmaceutical composition or as parts of separate compositions that are administered within a time interval that allows the peptide, the peptide construct, the conjugate molecule, or the pharmaceutical composition to enhance the immune response against the immunogen, i.e. co-administration is used in the same way as in connection with vaccine administration.

The antibody production may entail further steps of preparing monoclonal antibodies via methods known per se.

Aspects Relating to Nucleic Acids of the Invention

Instead of administering peptides, peptide constructs, conjugate molecules, and compositions comprising these, in order to induce an immunostimulatory effect, it is also possible to effect expression by somatic cells of those peptides, peptide constructs and conjugate molecules that can be expressed by a cell from a nucleic acid, such as a DNA or RNA molecule. For this purpose, an encoding nucleic acid is used in a manner equivalent to a nucleic acid vaccine that can accomplish transient expression of an immunogen after injection of the nucleic acid into a suitable cell.

For instance, it is within the scope of the present invention to administer vectors that cause expression of both an immunogen and the peptide, peptide construct, or conjugate molecule in the subject to whom the nucleic acid has been administered, thereby obtaining a simultaneous immunisation and adjuvant effect.

Hence the invention also provides a nucleic acid (such as DNA or RNA) encoding a peptide, a peptide construct, or a conjugate of the invention, provided that the peptide, a peptide construct, or a conjugate can in fact be encoded by a nucleic acid and expressed by a (human) cell. Hence, the nucleic acid is typically part vector, preferably an expression vector, such as naked DNA or RNA, DNA or RNA formulated in liposomes, a virus (attenuated) or a bacterium (attenuated).

The nucleic acid of the invention can hence be used to enhance immunogenicity of an immunogen, to stimulate (such as innate) immunity, or to enhance the effect of cancer immunotherapy or cancer chemotherapy.

PREAMBLE TO EXAMPLES

Procedure for IL-6, TNF-alpha and IL-1 Beta ELISA Quantification used in Examples 2, 4, and 5

ELISA assays were performed according to the manufacturer's protocol, as follows:

Each incubation step was followed by sealing and shaking on a rotating table at 150-200 rpm, except the overnight incubation with Capture Antibodies, where plates were not shaken. One day prior running ELISA, the 96-well assay plates were covered with the Capture Antibodies, here Capture IL-6 antibody or Capture TNF-alpha antibody or Capture IL-1 Beta antibody, diluted 1:200 in 1× Coating Buffer (5× Coating Buffer diluted in ddH2O). 100 µL of each of those Capture Antibodies solutions were added into all wells, sealed and incubated overnight (16-18 hrs) at 4° C. The next day all reagents from the set were brought to room temperature (RT) before use. The plates were washed 4 times with minimum 300 µL Wash Buffer (1×PBS, 0.05% Tween 20) per well. The residual buffer in the following washing was removed by blotting the plates against the absorbent paper. Next 200 µL of the 1× Assay Diluent A (5× Assay Diluent A diluted in PBS pH=7.4) was added for 1 h to block non specific binding. While the plates were being blocked, all samples and standards (mandatory for each plate) were prepared. Standards and samples were run in triplicates. For IL-6, 1 mL of the top standard concentration (250 pg/mL IL-6 quantification) was prepared in 1× Assay Diluent A (1×AD) from the IL-6 stock solution. The six two-fold serial dilutions of the 250 pg/mL top standard were performed, with the human IL-6, standard concentration: 250 pg/mL, 125 pg/mL, 62.5 pg/mL, 31.2 pg/mL, 15.6 pg/mL and 7.8 pg/mL. For TNF-alpha, 1 mL of the top standard concentration (500 pg/mL TNF-alpha quantification) was prepared in 1× Assay Diluent A (1×AD) from the TNF-alpha stock solution. The six two-fold serial dilutions of the 500 pg/mL top standard were performed, with the human TNF-alpha, standard concentration: 500 pg/mL, 250 pg/ml, 125 pg/mL, 62.5 pg/mL, 31.2 pg/mL, 15.6 pg/mL and 7.8 pg/mL. For IL-1 Beta, 1 mL of the top standard concentration (250 pg/mL IL-1 Beta quantification) was prepared in 1× Assay Diluent A (1×AD) from the IL-1 Beta stock solution. The six two-fold serial dilutions of the 250 pg/mL top standard were performed, with the human IL-1 Beta, standard concentration: 250 pg/mL, 125 pg/mL, 62.5 pg/mL, 31.2 pg/mL, 15.6 pg/mL and 7.8 pg/mL. 1×AD serves as the zero standard (0 pg/mL) for all examples, here Example 1, Example 2 and Example 3. After blocking the plates, washing was performed and 100 µL standards and samples were assayed in triplicates and incubated for 2 h in RT. Samples were not diluted for IL-6 analysis, diluted 5 fold for TNF-alpha analysis, or diluted 3 fold for IL-1 beta analysis. After washing, 100 µL of the IL-6 or TNF-alpha or IL-1 Beta Detection Antibody was applied to each well, diluted 1:200 in 1×AD, and incubated for 1 hour. Plates were washed and followed by 30 minutes incubation with 100 µL of Avidin-HRP solution per well, diluted 1:1000 in 1×AD. The final washing was performed 5 times with at least 30 seconds interval between the washings, to decrease the background. Next 100 µL of the freshly mixed TMB Substrate Solution (10 mL per plate, 5 mL of each from substrates provided in the set) was applied and left in the dark for 15 min. It needs to be observed to prevent signal saturation, positive wells turned blue. After incubation in the dark the reactions were stopped with 100 µL of 2 N H2SO4 per well. Positive wells turned yellow. Absorbance was measured at 450 nm and 570 nm (background) within 30 minutes. The data were analyzed in the Microsoft Excel 2010 program. Statistical analyses were performed using Microsoft Excel 2010 program.

Example 1

Immunomodulatory Function Induced by SG #4, SG #8, SG #13, and SG #14 (Derived from SEQ ID NOs: 2-5).

Pre-treatment of cells with peptides SG #4, SG #8, SG #13, and SG #14 (SEQ ID NOs: 2-5) promotes the release of cytokines, including pro-inflammatory cytokines such as IL-6, TNF-alpha, and IL-8.

The modulatory function of peptides SG #4, SG #8, SG #13, and SG #14 on the expression levels of IL-6 in the human acute monocytic leukaemia cell line THP-1 was examined. THP-1 cells were maintained in RPMI 1640 supplemented with 10% FBS, 100 U/ml penicillin, 100 µg/ml streptomycin and 2 mM L-glutamine at 37° C. in a 5% $CO_2$ incubator. THP-1 cells are known to induce IL-6, TNFα, IL-10 and IL-8 mRNA and protein in response to lipopolysaccharide (LPS) treatment. THP-1 cells were left untreated or incubated with 0 uM, 7.5 µM, 15 µM, 30 µM, 60 µM or 100 µm of each of the peptides, and stimulated with 1 µg/µl LPS for 6 h, based on previous analyses to find the optimal dose and incubation times.

Table 1: Modulatory function of peptides SG #4, SG #8, SG #13, and SG #14 on the expression levels of IL-6 in human acute monocytic leukaemia cell line THP-1.

(−) inhibition indicates percentage (%) of inhibition as compared to only LPS treated samples (arbitrarily set at 100%). As such (−)5.28609 for SG #13 at 30 µM indicates that compared to only LPS treated cells, 5.38609% of IL-6 secretion was inhibited (or, put differently, less than 95% of the IL-6 secretion observed from the only LPS treated cells was observed in the treated cells). Accordingly (+)36.9828% for SG #13 at 100 µM indicates that the level of secreted cytokine was 36.9828% above the only LPS treated samples (100%) or 136.98285% of the control.

TABLE 1

| | % IL-6 secretion level compared to LPS-stimulated control | | | | |
|---|---|---|---|---|---|
| | Conc. | | | | |
| Name | 7.5 µM | 15 µM | 30 µM | 60 µM | 100 µM |
| SG#1 | +0.68420 | +7.190170 | −3.53917 | −25.113390 | −26.67839 |
| SG#4 | +12.98853 | +20.763080 | +38.19179 | +36.394360 | +13.26897 |
| SG#8 | +1.471583 | +14.540560 | +6.835367 | +7.654897 | +20.85891 |
| SG#13 | −5.764790 | +6.907031 | −5.286090 | +8.616429 | +36.98280 |
| SG#14 | −2.981080 | −0.447620 | +0.740257 | +28.516960 | +15.20844 |

Example 2

Immunomodulatory Function Induced by SG #4, SG #22, SG #23, SG #24, SG #27, and SG #28.

Treatment of cells with any of the peptide constructs SG #4, SG #22, SG #23, SG #24, SG #27, and SG #28 affects the release of the pro-inflammatory cytokine IL-6.

Here, we examined the modulatory function of peptides, peptides SG #4, SG #22, SG #23, SG #24, SG #27, and SG #28 on the levels of IL-6 protein in human acute monocytic leukemia cell line THP-1. THP-1 cells were maintained in RPMI 1640 supplemented with 10% FBS, 100 U/ml penicillin, 100 μg/ml streptomycin and 2 mM L-glutamine at 37° C. in a 5% $CO_2$ incubator. THP-1 cells are known to induce IL-6 protein in response to lipopolysaccharide (LPS) treatment. THP-1 cells were left untreated or incubated with 0 μM, 15 μM, 30 μM, 60 μM of each of the peptide constructs SG #4, SG #22, SG #23, SG #24, SG #27, and SG #28, and stimulated with 1 μg/μl LPS for 24 h, based on the previous analyses to find the optimal dose and incubation times.

IL-6 ELISA Quantification

An ELISA assay was performed as described in the preamble to the examples. The results are shown in FIG. 1 and in Table 2.

Table 2: Activator function of peptide constructs SG #4, SG #22, SG #23, SG #24, SG #27, and SG #28 on the secretion levels of IL-6 in human acute monocytic leukemia cell line. As such (+) 35.0033 percentage (%) for SG #23 at 15 μM indicates that the level of secreted cytokine was 35.0033 percentage (%) above LPS-only treated samples (100%), that is 135.0033% of the baseline value.

TABLE 2

% IL-6 secretion level compared to LPS-stimulated control

| Name | 15 μM | 30 μM | 60 μM |
|---|---|---|---|
| | | Conc. | |
| SG#4 | (+) 20.2700 | (+) 29.7297 | (+) 40.2680 |
| SG#22 | (+) 19.1904 | (+) 23.0300 | (+) 26.6660 |

TABLE 2-continued

% IL-6 secretion level compared to LPS-stimulated control

| Name | 15 μM | 30 μM | 60 μM |
|---|---|---|---|
| | | Conc. | |
| SG#23 | (+) 35.0033 | (+) 27.5218 | (+) 25.6350 |
| SG#24 | (+) 40.4893 | (+) 60.66 | (+) 45.4972 |
| SG#27 | (+) 9.8445 | (+) 15.3867 | (+) 8.9126 |
| SG#28 | (+) 3.7390 | (+) 0 | (+) 5.6381 |

Example 3

Activation of Immune Response After In Vivo Immunization of Mice by Peptide Construct SG #4

Chicken ovalbumin has been used to trigger T cell activation in immunology studies. Ovalbumin immunized mice produce anti-OVA antibodies predominantly of the $IgG_1$ and IgE isotypes that mediate tissue-specific effector functions in multiple mouse models. Thus, it is often desirable to measure anti-OVA antibody levels in the plasma or serum to determine the effectiveness of the immunization/induction of a TH2-mediated immune response. Here, we tested the effectiveness of the SG #4 peptide in inducing of a TH2-mediated immune response in female BALB/c mice. The study agents contained Ovalbumin alone, peptide construct SG #4 alone or ovalbumin in combination with SG #4.

The study was composed of 4 groups of 5 mice each (5 female BALB/c mice). Animals were immunized at day 1 and day 14 using standard route of administration and following dosage listed in Table 3.

TABLE 3

Schedule for immunization of animals

| Procedure | Schedule | Route |
|---|---|---|
| Primary Immunization | T = 1 days | s.c. |
| 1st Boost | T = 14 days | s.c. |
| Test bleed | T = 21 days | Collect 15 ul antiserum/mouse |

TABLE 4

Groups included in the study, denomination, dose level, dose volume, treatment and number of animals.

| Group | Denomination | Dose level/ concentrations (μg/injection) | Dose volume (mL/injection) | Treatment/ Route over the study period | # of animals |
|---|---|---|---|---|---|
| 1 | Vehicle (NaCl or PBS) | 0 | 0.3 ml = 300 μl | Subcutaneously Day 1 and Day 14 | 5 |
| 2 | Ovalbumin | Primary immunization 50 μg/animal 1st Boost 25 μg/animal | 300 μl | Subcutaneously Day 1 and Day 14 | 5 |
| 3 | SG#4 | Primary immunization 5 μg/animal 1st Boost 5 μg/animal | (150 μl SG#4 + 150 μl of NaCl/PBS), total volume 300 μl | Subcutaneously Day 1 and Day 14 | 5 |

TABLE 4-continued

Groups included in the study, denomination, dose level, dose volume, treatment and number of animals.

| Group | Denomination | Dose level/ concentrations (μg/injection) | Dose volume (mL/injection) | Treatment/ Route over the study period | # of animals |
|---|---|---|---|---|---|
| 4 | SG#4 and ovalbumin | Primary immunization 50 μg/animal ovalbumin + 5 μg/animal SG#4 1st Boost 25 μg/animal ovalbumin + 5 μg/animal SG#4 | (150 μl of ovalbumin + 150 μl of SG#4) | Subcutaneously Day 1 and Day 14 | 5 |

Procedure for Anti-ovalbumin IgG$_1$ ELISA Quantification

An ELISA assay was carried out according to the manufacturer's protocol, as follows. Each well of the microwell plate supplied in the ELISA was coated with ovalbumin. Antibodies specific for ovalbumin, if present in the biological fluid, here 5 μl of serum from each mouse, will bind to the immobilized ovalbumin. A detection antibody recognizing mouse IgG$_1$ was added to the well. This Goat Anti-mouse IgG$_1$ was labeled with HRP, allowing quantification of the autoantibodies. Addition of the HRP Substrate 3,3', 5,5'-tetramethylbenzidine (TMB), following by Stop Solution produces a yellow colored product which was measured spectrophotometrically. The intensity of the color is directly proportional to the amount of bound goat anti-mouse IgG$_1$/HRP, which is proportional to the concentration of the anti-ovalbumin antibody. 1 mL of the top standard concentration (250 pg/mL anti-ovalbumin IgG$_1$ quantification) was prepared in 1× Assay Diluent A (1×AD) from the anti-ovalbumin IgG$_1$ stock solution. The six two-fold serial dilutions of the 250 pg/mL top standard were performed, with the human anti-ovalbumin IgG$_1$, standard concentration: 250 pg/mL, 125 pg/mL, 62.5 pg/mL, 31.2 pg/mL, 15.6 pg/mL, 7.8 pg/mL and 3.9 pg/mL. 1×AD serves as the zero standard (0 pg/mL). Calculations were performed by plotting the standard curve and determining the sample concentrations. Using computer reduction software, absorbance (linear y-axis) for standard versus concentration (linear x-axis) is plotted and data is fitted with a quadratic equation. Using the equation of the line, concentration of anti-ovalbumin IgG$_1$ in each serum sample was calculated. See FIG. 2 for the results.

As is clear from FIG. 2, after the second boost the group immunized with both SG #4 and ovalbumin showed a significantly higher induction of immune response as compared to animals immunized with ovalbumin alone. Measurement of anti-OVA IgG$_1$ was used as a method of assessing the magnitude of the TH2 immune response mediated by peptide, peptide SG #4.

Example 4

Immunomodulatory Function Induced by SG #4, SG #22, SG #23, SG #24, and SG #28.

Treatment of cells with any of the peptides SG #4, SG #22, SG #23, SG #24, and SG #28 affects the release of pro-inflammatory cytokine TNF-alpha.

Here, we examined the modulatory function of peptides, peptides SG #4, SG #22, SG #23, SG #24, and SG #28 on the levels of TNF-alpha protein in the human acute monocytic leukemia cell line THP-1. THP-1 cells were maintained in RPMI 1640 supplemented with 10% FBS, 100 U/ml penicillin, 100 μg/ml streptomycin and 2 mM L-glutamine at 37° C. in a 5% CO$_2$ incubator. THP-1 cells are known to induce TNF-alpha protein in response to lipopolysaccharide (LPS) treatment.

THP-1 cells were left untreated or incubated with 0 uM, 15 μM, 30 μM, of each of the peptide constructs SG #4, SG #22, SG #23, SG #24, and SG #28 and stimulated with 1 μg/μl LPS for 24 h, based on the previous analyses to find the optimal dose and incubation times.

TNF-alpha ELISA quantification

An ELISA assay was performed as described in the preamble to the examples. The results are shown in FIG. 3 and in Table 5.

TABLE 5

Activator function of peptides, peptides SG#4, SG#22, SG#23, SG#24, and SG #28 on the secretion levels of TNF-alpha in human acute monocytic leukemia cell line. As such (+) 83.64 percentage (%) for SG#4 at 15 μM indicates that the median level of secreted cytokine was 83.64 percentage (%) above the only LPS treated samples (100%) or 183.64.

% TNF-alpha secretion level compared to LPS-stimulated control

| | Concentration | |
|---|---|---|
| Name | 15 μM | 30 μM |
| SG#4 | (+) 83.64 | (+) 237.956 |
| SG#22 | (+) 1.605 | (+) 116.3503 |
| SG#23 | (+) 34.0145 | (+) 262.0437 |
| SG#24 | (+) 11.5036 | (+) 279.2700 |
| SG#28 | (+) 11.2408 | (+) 97.0802 |

Example 5

Immunomodulatory function induced by SG #4, SG #22, SG #23, SG #24, and SG #28.

Treatment of cells with any of the peptide constructs SG #4, SG #22, SG #23, SG #24, and SG #28 affects the release of pro-inflammatory cytokine IL-1 Beta.

Here, we examined the modulatory function of peptide constructs SG #4, SG #22, SG #23, SG #24, and SG #28 on the levels of IL-1 Beta protein in human acute monocytic leukemia cell line THP-1. THP-1 cells were maintained in RPMI 1640 supplemented with 10% FBS, 100 U/ml penicillin, 100 μg/ml streptomycin and 2 mM L-glutamine at 37° C. in a 5% CO2 incubator. THP-1 cells are known to induce IL-1 Beta protein in response to lipopolysaccharide (LPS) treatment. THP-1 cells were left untreated or incubated with 0 uM, 15 μM, 30 μM, of each of the peptide constructs SG

4, SG #22, SG #23, SG #24, and SG #28 and stimulated with 1 μg/μl LPS for 24 h, based on the previous analyses to find the optimal dose and incubation times.

IL-1 Beta ELISA Quantification

An ELISA assay was performed as described in the preamble to the examples. The results are shown in FIG. 4 and in Table 6.

TABLE 6

Activator function of peptides, peptides SG#4, SG#22, SG#23, SG#24, and SG #28 on the secretion levels of IL-1 Beta in human acute monocytic leukemia cell line. As such (+) 44.44 percentage (%) for SG#4 at 15 μM indicates that the median level of secreted cytokine was 44.44 percentage (%) above the only LPS treated samples (100%) or 144.44.
% IL-1 Beta secretion level compared to LPS-stimulated control

| | Concentration | |
|---|---|---|
| Name | 15 μM | 30 μM |
| SG#4 | (+) 44.444 | (+) 175.661 |
| SG#22 | (+) 35.978 | (+) 80.158 |

TABLE 6-continued

Activator function of peptides, peptides SG#4, SG#22, SG#23, SG#24, and SG #28 on the secretion levels of IL-1 Beta in human acute monocytic leukemia cell line. As such (+) 44.44 percentage (%) for SG#4 at 15 μM indicates that the median level of secreted cytokine was 44.44 percentage (%) above the only LPS treated samples (100%) or 144.44.
% IL-1 Beta secretion level compared to LPS-stimulated control

| | Concentration | |
|---|---|---|
| Name | 15 μM | 30 μM |
| SG#23 | (+) 59.259 | (+) 130.158 |
| SG#24 | (−) 18.5396 | (+) 220.6349 |
| SG#28 | (+) 53.9682 | (+) 93.650 |

The invention claimed is:

1. A peptide consisting of or comprising a sequence variant of the amino acid sequence LQNRRGLGLSILLNEEC (SEQ ID NO: 1), wherein the sequence variant comprises at least one amino acid change compared to SEQ ID NO: 1 in any one of residues 1-7 and 15-17 but no amino acid changes in residues 8-14, and wherein the peptide stimulates secretion and/or expression of cytokines when supplied in an effective concentration to THP-1 cells or PBMCs stimulated with lipopolysaccharide (LPS) and wherein a C-terminal carboxyl group is modified.

2. The peptide according to claim 1, wherein the C-terminal carboxyl group is modified by amidation.

3. The peptide according to claim 1, wherein the net charge of the peptide at neutral pH is increased compared to the net charge of the peptide having the amino acid sequence SEQ ID NO: 1.

4. The peptide according to claim 1, wherein the amino acid change(s) is/are independently selected from substitution, deletion, and insertion.

5. The peptide according to claim 1, wherein the sequence variant comprises 1, 2, or 3 amino acid change(s) in positions 15-17 of SEQ ID NO: 1.

6. The peptide according to claim 5, wherein the amino acid change is deletion of one or more of residues 15-17.

7. The peptide according to claim 1, wherein the sequence variant comprises an amino acid change in position 4 of SEQ ID NO: 1.

8. The peptide according to claim 7, wherein the amino acid change of position 4 is a substitution.

9. The peptide according to claim 8, wherein the amino acid change in position 4 is a substitution with an amino acid residue selected from the group consisting of amino acids that increase the charge at neutral pH of the peptide compared to SEQ ID NO: 1.

10. The peptide according to claim 9, wherein position 4 in SEQ ID NO: 1 is substituted with a Lysine residue.

11. The peptide according to claim 1, wherein the sequence variant comprises an amino acid change in position 5 of SEQ ID NO: 1.

12. The peptide according to claim 11, wherein the amino acid change of position 5 is a substitution.

13. The peptide according to claim 12, wherein the amino acid change in position 5 is substitution with an amino acid residue selected from the group consisting of amino acids that increases the charge at neutral pH of the peptide compared to SEQ ID NO: 1.

14. The peptide according to claim 13, wherein position 5 in SEQ ID NO: 1 is substituted with a Lysine residue.

15. The peptide according to claim 1, which has the formula I $$Z^1Z^2Z^3X^1X^2Z^4Z^5GLSILLNX^3X^4X^5 \quad (I)$$

(SEQ ID NO: 8)

wherein $Z^1$ is L or absent,
$Z^2$ is Q or absent,
$Z^3$ is N or absent,
$Z^4$, is G or absent,
$Z^5$ is L or absent,
$X^1$ is R or K or absent,
$X^2$ is R or K or absent,
$X^3$ is E or absent,
$X^4$ is E or absent, and
$X^5$ is C or absent,
with the proviso that Formula I does not have the amino acid sequence SEQ ID NO: 1.

16. The peptide according to claim 15, wherein
if $Z^1$ is present then $Z^2$-$Z^5$, $X^1$, and $X^2$ are all present;
if $Z^2$ is present, then $Z^3$-$Z^5$, $X^1$, and $X^2$ are all present;
if $Z^3$ is present, then $Z^4$ and $Z^5$, $X^1$, and $X^2$ are all present;
if $Z^4$ is present, then $Z^5$, $X^1$, and $X^2$ are all present; or
if $X^1$ is present, then $X^2$ is present.

17. The peptide according to claim 16, wherein
$Z^1$ is absent, or
$Z^2$ is absent, or
$Z^3$ is absent, or
$Z^4$ is absent, or
$Z^5$ is absent, or
$X^1$ is absent, or
$X^2$ is absent.

18. The peptide according to claim 17, wherein
$Z^1$ is present, or
$Z^2$ is present, or
$Z^3$ is present, or
$Z^4$ is present, or
$Z^5$ is present, or
$X^1$ is present, or
$X^2$ is present.

19. The peptide according to claim 16, wherein
$Z^1$ is present, or
$Z^2$ is present, or
$Z^3$ is present, or
$Z^4$ is present, or
$Z^5$ is present, or
$X^1$ is present, or
$X^2$ is present.

20. The peptide according to claim 15, wherein
$X^3$, $X^4$, and $X^5$ are all present, or
only one of $X^3$ and $X^4$ is present and $X^5$ is present, or
only $X^5$ is present, or
none of $X^3$-$X^5$ is present.

21. The peptide according to claim 1, which has the amino acid sequence set forth in any one of SEQ ID NOs: 2-7 and 9.

22. A method for preparation of antibodies that specifically binds an immunogen, the method comprising co-administration to an animal of an immunogenically active amount of
 a peptide according to claim 1, and
 the immunogen,
so as to effect production of antibodies specific for said immunogen in said animal, and subsequently recovering said antibodies from the animal.

23. A pharmaceutical composition comprising a peptide consisting of or comprising a sequence variant of the amino acid sequence LQNRRGLGLSILLNEEC (SEQ ID NO: 1), wherein the sequence variant comprises at least one amino acid change compared to SEQ ID NO: 1 in any one of residues 1-7 and 15-17 but no amino acid changes in residues 8-14, wherein the peptide stimulates secretion and/or expression of cytokines when supplied in an effective concentration to THP-1 cells or PBMCs stimulated with lipopolysaccharide (LPS), and wherein said composition further comprises a pharmaceutically acceptable carrier, diluent or excipient.

24. The pharmaceutical composition according to claim 23, which in addition comprises an immunogen.

25. A peptide consisting of or comprising a sequence variant of the amino acid sequence LQNRRGLGLSILL-NEEC (SEQ ID NO: 1), wherein the sequence variant comprises at least one amino acid change compared to SEQ ID NO: 1 in any one of residues 1-7 and 15-17 but no amino acid changes in residues 8-14, and wherein the peptide stimulates secretion and/or expression of cytokines when supplied in an effective concentration to THP-1 cells or PBMCs stimulated with lipopolysaccharide (LPS) and wherein the sequence variant comprises deletion of one or more of residues 15-17.

26. The peptide according to claim 25, wherein the net charge of the peptide at neutral pH is increased compared to the net charge of the peptide having the amino acid sequence SEQ ID NO: 1.

27. The peptide according to claim 25, wherein the amino acid change(s) is/are independently selected from substitution, deletion, and insertion.

28. The peptide according to claim 25, wherein the sequence variant comprises an amino acid change in position 4 of SEQ ID NO: 1.

29. The peptide according to claim 28, wherein the amino acid change of position 4 is a substitution.

30. The peptide according to claim 29, wherein the amino acid change in position 4 is substitution with an amino acid residue selected from the group consisting of amino acids that increase the charge at neutral pH of the peptide compared to SEQ ID NO: 1.

31. The peptide according to claim 30, wherein position 4 in SEQ ID NO: 1 is substituted with a Lysine residue.

32. The peptide according to claim 25, wherein the sequence variant comprises an amino acid change in position 5 of SEQ ID NO: 1.

33. The peptide according to claim 32, wherein the amino acid change of position 5 is a substitution.

34. The peptide according to claim 33, wherein the amino acid change in position 5 is substitution with an amino acid residue selected from the group consisting of amino acids that increase the charge at neutral pH of the peptide compared to SEQ ID NO: 1.

35. The peptide according to claim 34, wherein position 5 in SEQ ID NO: 1 is substituted with a Lysine residue.

36. A method for preparation of antibodies that specifically bind an immunogen, the method comprising co-administration to an animal an immunogenically active amount of
 a peptide according to claim 25, and
 the immunogen,
so as to effect production of antibodies specific for said immunogen in said animal, and subsequently recovering said antibodies from the animal.

37. A peptide consisting of or comprising a sequence variant of the amino acid sequence LQNRRGLGLSILL-NEEC (SEQ ID NO: 1), wherein the sequence variant comprises at least one amino acid change compared to SEQ ID NO: 1 in any one of residues 1-7 and 15-17 but no amino acid changes in residues 8-14, and wherein the peptide stimulates secretion and/or expression of cytokines when supplied in an effective concentration to THP-1 cells or PBMCs stimulated with lipopolysaccharide (LPS) and wherein the amino acid in position 4 is substituted with an amino acid residue selected from the group of amino acids that increase the charge at neutral pH of the peptide compared to SEQ ID NO: 1.

38. The peptide according to claim 37, wherein position 4 in SEQ ID NO: 1 is substituted with a Lysine residue.

39. The peptide according to claim 37, wherein the sequence variant comprises an amino acid change in position 5 of SEQ ID NO: 1.

40. The peptide according to claim 39, wherein the amino acid change of position 5 is a substitution.

41. The peptide according to claim 40, wherein the amino acid change in position 5 is substitution with an amino acid residue selected from the group consisting of amino acids that increase the charge at neutral pH of the peptide compared to SEQ ID NO: 1.

42. The peptide according to claim 41, wherein position 5 in SEQ ID NO: 1 is substituted with a Lysine residue.

43. A method for preparation of antibodies that specifically bind an immunogen, the method comprising co-administration to an animal an immunogenically active amount of
 a peptide according to claim 37, and
 the immunogen,
so as to effect production of antibodies specific for said immunogen in said animal, and subsequently recovering said antibodies from the animal.

44. A peptide consisting of or comprising a sequence variant of the amino acid sequence LQNRRGLGLSILL-NEEC (SEQ ID NO: 1), wherein the sequence variant comprises at least one amino acid change compared to SEQ ID NO: 1 in any one of residues 1-7 and 15-17 but no amino acid changes in residues 8-14, and wherein the peptide stimulates secretion and/or expression of cytokines when supplied in an effective concentration to THP-1 cells or PBMCs stimulated with lipopolysaccharide (LPS)
 wherein the peptide has the formula I $$Z^1Z^2Z^3X^1X^2\ Z^4\ Z^5GLSILLNX^3X^4X^5 \quad \text{(I)} \quad \text{(SEQ ID NO: 8)}$$

wherein
 $Z^1$ is L or absent,
 $Z^2$ is Q or absent,
 $Z^3$ is N or absent,
 $Z^4$, is G or absent,
 $Z^5$ is L or absent,
 $X^1$ is R or K or absent, $X^2$ is R or K or absent,
$X^3$ is E or absent,
$X^4$ is E or absent, and
$X^5$ is C or absent,
with the proviso that Formula I does not have the amino acid sequence SEQ ID NO: 1,
and wherein
  if $Z^1$ is present then $Z^2$-$Z^5$, $X^1$, and $X^2$ are all present;
  if $Z^2$ is present, then $Z^3$-$Z^5$, $X^1$, and $X^2$ are all present;
  if $Z^3$ is present, then $Z^4$ and $Z^5$, $X^1$, and $X^2$ are all present;
  if $Z^4$ is present, then $Z^5$, $X^1$, and $X^2$ are all present; and
  if $X^1$ is present, then $X^2$ is present,
and wherein
  $Z^1$ is present, or
  $Z^2$ is present, or
  $Z^3$ is present, or
  $Z^4$ is present, or
  $Z^5$ is present, or
  $X^1$ is present, or
  $X^2$ is present.

45. The peptide according to claim 6, which comprises deletion of one or both of residues 15 and 16 or deletion of residue 17.

46. A pharmaceutical composition comprising a peptide selected from the group consisting of
  a peptide consisting of or comprising a sequence variant of the amino acid sequence LQNRRGLGLSILLNEEC (SEQ ID NO: 1), wherein the sequence variant comprises at least one amino acid change compared to SEQ ID NO: 1 in any one of residues 1-7 and 15-17 but no amino acid changes in residues 8-14, and wherein the peptide stimulates secretion and/or expression of cytokines when supplied in an effective concentration to THP-1 cells or PBMCs stimulated with lipopolysaccharide (LPS) and wherein the sequence variant comprises deletion of one or more of residues 15-17;
  a peptide consisting of or comprising a sequence variant of the amino acid sequence LQNRRGLGLSILLNEEC (SEQ ID NO: 1), wherein the sequence variant comprises at least one amino acid change compared to SEQ ID NO: 1 in any one of residues 1-7 and 15-17 but no amino acid changes in residues 8-14, and wherein the peptide stimulates secretion and/or expression of cytokines when supplied in an effective concentration to THP-1 cells or PBMCs stimulated with lipopolysaccharide (LPS) and wherein the amino acid in position 4 is substituted with an amino acid residue selected from the group of amino acids that increase the charge at neutral pH of the peptide compared to SEQ ID NO: 1; and
  a peptide consisting of or comprising a sequence variant of the amino acid sequence LQNRRGLGLSILLNEEC (SEQ ID NO: 1), wherein the sequence variant comprises at least one amino acid change compared to SEQ ID NO: 1 in any one of residues 1-7 and 15-17 but no amino acid changes in residues 8-14, and wherein the peptide stimulates secretion and/or expression of cytokines when supplied in an effective concentration to THP-1 cells or PBMCs stimulated with lipopolysaccharide (LPS)
wherein the peptide has the formula I (I)
(SEQ ID NO: 8)
$$Z^1Z^2Z^3X^1X^2\ Z^4\ Z^5GLSILLNX^3X^4X^5$$

wherein
  $Z^1$ is L or absent,
  $Z^2$ is Q or absent,
  $Z^3$ is N or absent,
  $Z^4$, is G or absent,
  $Z^5$ is L or absent,
  $X^1$ is R or K or absent,
  $X^2$ is R or K or absent,
  $X^3$ is E or absent,
  $X^4$ is E or absent, and
  $X^5$ is C or absent,
with the proviso that Formula I does not have the amino acid sequence SEQ ID NO: 1,
and wherein
  if $Z^1$ is present then $Z^2$-$Z^5$, $X^1$, and $X^2$ are all present;
  if $Z^2$ is present, then $Z^3$-$Z^5$, $X^1$, and $X^2$ are all present;
  if $Z^3$ is present, then $Z^4$ and $Z^5$, $X^1$, and $X^2$ are all present;
  if $Z^4$ is present, then $Z^5$, $X^1$, and $X^2$ are all present; and
  if $X^1$ is present, then $X^2$ is present,
and wherein
  $Z^1$ is present, or
  $Z^2$ is present, or
  $Z^3$ is present, or
  $Z^4$ is present, or
  $Z^5$ is present, or
  $X^1$ is present, or
  $X^2$ is present.

47. A method for preparation of antibodies that specifically binds an immunogen, the method comprising co-administration to an animal an immunogenically active amount of
  a peptide according to claim 44, and
  the immunogen,
so as to effect production of antibodies specific for said immunogen in said animal, and subsequently recovering said antibodies from the animal.

* * * * *

SEQUENCE LISTING

```
<160> NUMBER OF SEQ ID NOS: 12

<210> SEQ ID NO 1
<211> LENGTH: 17
<212> TYPE: PRT
<213> ORGANISM: Homo sapiens

<400> SEQUENCE: 1

Leu Gln Asn Arg Arg Gly Leu Gly Leu Ser Ile Leu Leu Asn Glu Glu
1               5                   10                  15

Cys

<210> SEQ ID NO 2
<211> LENGTH: 15
<212> TYPE: PRT
<213> ORGANISM: Artificial sequence
<220> FEATURE:
<223> OTHER INFORMATION: Mutated sequence

<400> SEQUENCE: 2

Leu Gln Asn Arg Arg Gly Leu Gly Leu Ser Ile Leu Leu Asn Cys
1               5                   10                  15

<210> SEQ ID NO 3
<211> LENGTH: 23
<212> TYPE: PRT
<213> ORGANISM: Artificial sequence
<220> FEATURE:
<223> OTHER INFORMATION: Mutated sequence

<400> SEQUENCE: 3

Leu Gln Asn Lys Arg Gly Leu Gly Leu Ser Ile Leu Leu Asn Glu Glu
1               5                   10                  15

Cys Gly Pro Gly Pro Gly Pro
                20

<210> SEQ ID NO 4
<211> LENGTH: 16
<212> TYPE: PRT
<213> ORGANISM: Artificial sequence
<220> FEATURE:
<223> OTHER INFORMATION: Mutated sequence
```

-continued

```
<400> SEQUENCE: 4

Leu Gln Asn Arg Arg Gly Leu Gly Leu Ser Ile Leu Leu Asn Glu Glu
1               5                   10                  15

<210> SEQ ID NO 5
<211> LENGTH: 23
<212> TYPE: PRT
<213> ORGANISM: Artificial sequence
<220> FEATURE:
<223> OTHER INFORMATION: Mutated sequence

<400> SEQUENCE: 5

Leu Gln Asn Arg Arg Gly Leu Gly Leu Ser Ile Leu Leu Asn Glu Glu
1               5                   10                  15

Leu Gln Asn Arg Arg Gly Leu
            20

<210> SEQ ID NO 6
<211> LENGTH: 15
<212> TYPE: PRT
<213> ORGANISM: Artificial sequence
<220> FEATURE:
<223> OTHER INFORMATION: Mutated sequence

<400> SEQUENCE: 6

Leu Gln Asn Lys Arg Gly Leu Gly Leu Ser Ile Leu Leu Asn Cys
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: Mutated sequence

<400> SEQUENCE: 7

Leu Gln Asn Lys Lys Gly Leu Gly Leu Ser Ile Leu Leu Asn Cys
1               5                   10                  15

<210> SEQ ID NO 8
<211> LENGTH: 17
<212> TYPE: PRT
<213> ORGANISM: Artificial sequence
<220> FEATURE:
<223> OTHER INFORMATION: Mutated sequence
<220> FEATURE:
<221> NAME/KEY: MISC_FEATURE
<222> LOCATION: (4)..(5)
<223> OTHER INFORMATION: Xaa is Arg or Lys
<220> FEATURE:
<221> NAME/KEY: MISC_FEATURE
<222> LOCATION: (15)..(16)
<223> OTHER INFORMATION: Xaa is Glu or absent
<220> FEATURE:
<221> NAME/KEY: MISC_FEATURE
<222> LOCATION: (17)..(17)
<223> OTHER INFORMATION: Xaa is Cys or absent

<400> SEQUENCE: 8

Leu Gln Asn Xaa Xaa Gly Leu Gly Leu Ser Ile Leu Leu Asn Xaa Xaa
1               5                   10                  15

Xaa

<210> SEQ ID NO 9
<211> LENGTH: 9
<212> TYPE: PRT
<213> ORGANISM: Homo sapiens
```

<400> SEQUENCE: 9

Gly Leu Ser Ile Leu Leu Asn Glu Glu
1               5

<210> SEQ ID NO 10
<211> LENGTH: 17
<212> TYPE: PRT
<213> ORGANISM: Artificial sequence
<220> FEATURE:
<223> OTHER INFORMATION: Env 59 derived peptide
<220> FEATURE:
<221> NAME/KEY: MISC_FEATURE
<222> LOCATION: (1)..(1)
<223> OTHER INFORMATION: Xaa is Leu or absent
<220> FEATURE:
<221> NAME/KEY: MISC_FEATURE
<222> LOCATION: (2)..(2)
<223> OTHER INFORMATION: Xaa is Gln or absent
<220> FEATURE:
<221> NAME/KEY: MISC_FEATURE
<222> LOCATION: (3)..(3)
<223> OTHER INFORMATION: Xaa is Asn or absent
<220> FEATURE:
<221> NAME/KEY: MISC_FEATURE
<222> LOCATION: (4)..(4)
<223> OTHER INFORMATION: Xaa is Arg or Lys or absent
<220> FEATURE:
<221> NAME/KEY: MISC_FEATURE
<222> LOCATION: (5)..(5)
<223> OTHER INFORMATION: Xaa is Arg or Lys or absent
<220> FEATURE:
<221> NAME/KEY: MISC_FEATURE
<222> LOCATION: (6)..(6)
<223> OTHER INFORMATION: Xaa is Gly or absent
<220> FEATURE:
<221> NAME/KEY: MISC_FEATURE
<222> LOCATION: (7)..(7)
<223> OTHER INFORMATION: Xaa is Leu or absent
<220> FEATURE:
<221> NAME/KEY: MISC_FEATURE
<222> LOCATION: (15)..(15)
<223> OTHER INFORMATION: Xaa is Glu or absent
<220> FEATURE:
<221> NAME/KEY: MISC_FEATURE
<222> LOCATION: (16)..(16)
<223> OTHER INFORMATION: Xaa is Glu or absent
<220> FEATURE:
<221> NAME/KEY: MISC_FEATURE
<222> LOCATION: (17)..(17)
<223> OTHER INFORMATION: Xaa is Cys or absent

<400> SEQUENCE: 10

Xaa Xaa Xaa Xaa Xaa Xaa Xaa Gly Leu Ser Ile Leu Leu Asn Xaa Xaa
1               5                   10                  15

Xaa

<210> SEQ ID NO 11
<211> LENGTH: 7
<212> TYPE: PRT
<213> ORGANISM: Artificial sequence
<220> FEATURE:
<223> OTHER INFORMATION: Gly-Pro repeat

<400> SEQUENCE: 11

Cys Gly Pro Gly Pro Gly Pro
1               5

<210> SEQ ID NO 12
<211> LENGTH: 6
<212> TYPE: PRT
<213> ORGANISM: Artificial sequence

```
<220> FEATURE:
<223> OTHER INFORMATION: GP repeat

<400> SEQUENCE: 12

Gly Pro Gly Pro Gly Pro
1               5
```